US009770484B2

(12) United States Patent
Guinan et al.

(10) Patent No.: US 9,770,484 B2
(45) Date of Patent: Sep. 26, 2017

(54) BPI AND ITS CONGENERS AS RADIATION MITIGATORS AND RADIATION PROTECTORS

(71) Applicants: Dana-Farber Cancer Institute, Inc., Boston, MA (US); Children's Medical Center Corporation, Boston, MA (US)

(72) Inventors: Eva Guinan, Newton, MA (US); Ofer Levy, Jamaica Plain, MA (US)

(73) Assignees: Dana-Farber Cancer Institute, Inc., Boston, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/169,969

(22) Filed: Jun. 1, 2016

(65) Prior Publication Data
US 2017/0065676 A1  Mar. 9, 2017

Related U.S. Application Data

(62) Division of application No. 14/009,201, filed as application No. PCT/US2012/032288 on Apr. 5, 2012.

(60) Provisional application No. 61/471,896, filed on Apr. 5, 2011.

(51) Int. Cl.
| | |
|---|---|
| *A61K 38/00* | (2006.01) |
| *C07K 14/47* | (2006.01) |
| *A61K 38/17* | (2006.01) |
| *A61K 45/06* | (2006.01) |
| *A61K 31/4709* | (2006.01) |
| *A61K 31/496* | (2006.01) |
| *A61K 31/5383* | (2006.01) |

(52) U.S. Cl.
CPC ...... *A61K 38/1751* (2013.01); *A61K 31/4709* (2013.01); *A61K 31/496* (2013.01); *A61K 31/5383* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,420,019 | A | 5/1995 | Theofan et al. |
| 5,494,896 | A | 2/1996 | Hansbrough |
| 5,980,897 | A | 11/1999 | Elsbach et al. |
| 6,268,345 | B1 | 7/2001 | Grinna |
| 6,355,616 | B1 | 3/2002 | Little et al. |
| 6,599,880 | B1 | 7/2003 | Horwitz et al. |
| 2004/0265231 | A1 | 12/2004 | Blumenthal et al. |
| 2008/0031874 | A1 | 2/2008 | Sanders |
| 2009/0035781 | A1 | 2/2009 | Chien |
| 2014/0142024 | A1 | 5/2014 | Guinan et al. |

FOREIGN PATENT DOCUMENTS

| | | |
|---|---|---|
| WO | WO 98/19694 A1 | 5/1998 |
| WO | WO 00/59531 A2 | 10/2000 |
| WO | WO 01/00671 A1 | 1/2001 |

OTHER PUBLICATIONS

U.S. Appl. No. 15/169,966, filed Jun. 1, 2016, pending.
EP12767712.8, Aug. 18, 2014, Supplemental European Search Report.
PCT/US2012/32288, Aug. 3, 2012, International Search Report and Written Opinion.
PCT/US2012/32288, Oct. 17, 2013, International Preliminary Report on Patentability.
Supplementary European Search Report for EP12767712.8 dated Aug. 18, 2014.
International Search Report and Written Opinion for International Application No. PCT/US2012/32288 dated Aug. 3, 2012.
International Preliminary Report on Patentability for International Application No. PCT/US2012/32288 dated Oct. 17, 2013.
[No Author Listed], XOMA Initiates Clinical Trial of NEUPREX At Harvard Medical School in Allogeneic Hematopoietic Stem Cell Transplantation. XOMA Corporation. XP002727112. Jan. 9, 2007. http://globenewswire.com/news-release/2007/01/09/353306/111542/en/XOMA-Initiates-Clinical-Trial-of-NEUPREX-At-Harvard-Medical-School-in-Allogeneic-Hematopoietic-Stem-Cell-Transplantation.html [last accessed Jul. 14, 2014].
Ainsworth, From endotoxins to newer immunomodulators: survival-promoting effects of microbial polysaccharide complexes in irradiated animals. Pharmacol Ther. 1988;39(1-3):223-41.
Anno et al., Symptomatology of acute radiation effects in humans after exposure to doses of 0.5-30 Gy. Health Phys. Jun. 1989;56(6):821-38.
Armand et al., Improved survival in lymphoma patients receiving sirolimus for graft-versus-host disease prophylaxis after allogeneic hematopoietic stem-cell transplantation with reduced-intensity conditioning. J Clin Oncol. Dec. 10, 2008;26(35):5767-74. doi: 10.1200/JCO.2008.17.7279. Epub Nov. 10, 2008.
Baranov et al., Bone marrow transplantation after the Chernobyl nuclear accident. N Engl J Med. Jul. 27, 1989;321(4):205-12.
Bauer et al., Pharmacokinetics of a recombinant modified amino terminal fragment of bactericidal/permeability-increasing protein (rBPI21) in healthy volunteers. J Clin Pharmacol. Nov. 1999;39(11):1169-76.
Bazil et al., Shedding as a mechanism of down-modulation of CD14 on stimulated human monocytes. J Immunol. Sep. 1, 1991;147(5):1567-74.
Beutler et al., Innate immune sensing and its roots: the story of endotoxin. Nat Rev Immunol. Feb. 2003;3(2):169-76.
Boggs et al., Effects of endotoxin on hematopoiesis in irradiated and nonirradiated W-Wv mice. Radiat Res. Dec. 1973;56(3):481-93.
Brook et al., Clindamycin and quinolone therapy for Bacillus anthracia Sterne infection in 60Co-gamma-photon-irradiated and sham-irradiated mice. J Antimicrob Chemother. Dec. 2005;56(6):1074-80. Epub Oct. 20, 2005.

(Continued)

*Primary Examiner* — Jeanette Lieb
(74) *Attorney, Agent, or Firm* — Wolf, Greenfield & Sacks, P.C.

(57) ABSTRACT

Described herein is a method of mitigating, in a subject (individual), tissue injury resulting from exposure to radiation (accidental/unintentional or intentional, such as therapeutic), chemoradiotherapy, disease, toxin, or drug or biologic mediated therapy.

18 Claims, 23 Drawing Sheets

(56) References Cited

OTHER PUBLICATIONS

Brook et al., Effect of antimicrobial therapy on bowel flora and bacterial infection in irradiated mice. Int J Radiat Biol Relat Stud Phys Chem Med. May 1988;53(5):709-16.
Brook et al., Quinolone therapy in the prevention of endogenous and exogenous infection after irradiation. J Antimicrob Chemother. Apr. 1994;33(4):777-84.
Burdelya et al., An agonist of toll-like receptor 5 has radioprotective activity in mouse and primate models. Science. Apr. 11, 2008;320(5873):226-30. doi: 10.1126/science.1154986.
Champlin, The role of bone marrow transplantation for nuclear accidents: implications of the Chernobyl disaster. Semin Hematol. Jul. 1987;24(3 Suppl 2):1-4.
Crawford et al., Microbial regulation of intestinal radiosensitivity. Proc Natl Acad Sci U S A. Sep. 13, 2005;102(37):13254-9. Epub Aug. 29, 2005.
Crenn et al., Citrulline as a biomarker of intestinal failure due to enterocyte mass reduction. Clin Nutr. Jun. 2008;27(3):328-39. doi: 10.1016/j.clnu.2008.02.005. Epub Apr. 28, 2008.
Dainiak et al., The evolving role of haematopoietic cell transplantation in radiation injury: potentials and limitations. BJR Suppl. 2005;27:169-74.
Demetriades et al., Bactericidal/permeability-increasing protein (rBPI21) in patients with hemorrhage due to trauma: results of a multicenter phase II clinical trial. rBPI21 Acute Hemorrhagic Trauma Study Group. J Trauma. Apr. 1999;46(4):667-76; discussion 676-7.
Gaffin et al., Anti-lipopolysaccharide toxin therapy for whole body X-irradiation overdose. Br J Radiol. Sep. 1985;58(693):881-4.
Garwicz et al., Biosynthetic profiles of neutrophil serine proteases in a human bone marrow-derived cellular myeloid differentiation model. Haematologica. Jan. 2005;90(1):38-44.
Gioannini et al., Regulation of interactions of Gram-negative bacterial endotoxins with mammalian cells. Immunol Res. 2007;39(1-3):249-60.
Giroir et al., Bactericidal/permeability-increasing protein—lessons learned from the phase III, randomized, clinical trial of rBPI21 for adjunctive treatment of children with severe meningococcemia. Crit Care Med. Jul. 2001;29(7 Suppl):S130-5.
Gomei et al., Functional differences between two Tie2 ligands, angiopoietin-1 and -2, in regulation of adult bone marrow hematopoietic stem cells. Exp Hematol. Feb. 2010;38(2):82-9. Epub Nov. 26, 2009.
Greenberger, Radioprotection. In Vivo. Mar.-Apr. 2009;23(2):323-36.
Guinan et al., Bactericidal/Permeability-Increasing Protein (rBPI21) and Fluoroquinolone Mitigate Radiation-Induced Bone Marrow Aplasia and Death. Science Translational Medicine. Nov. 2011;3(110):1-11.
Hammond et al., Effect of continuous gamma irradiation of mice on their leukocyte counts and susceptibility to bacterial infection. Radiat Res. Aug. 1959;11:242-52.
Hill et al., Total body irradiation and acute graft-versus-host disease: the role of gastrointestinal damage and inflammatory cytokines. Blood. Oct. 15, 1997;90(8):3204-13.
Iannini, The safety profile of moxifloxacin and other fluoroquinolones in special patient populations. Curr Med Res Opin. Jun. 2007;23(6):1403-13. Epub May 8, 2007.
Kiang et al., Wound trauma increases radiation-induced mortality by activation of iNOS pathway and elevation of cytokine concentrations and bacterial infection. Radiat Res. Mar. 2010;173(3):319-32. doi: 10.1667/RR1892.1.
Kim et al., High-throughput screening identifies two classes of antibiotics as radioprotectors: tetracyclines and fluoroquinolones. Clin Cancer Res. Dec. 1, 2009;15(23):7238-45. doi: 10.1158/1078-0432.CCR-09-1964. Epub Nov. 17, 2009.
Koenig et al., Medical treatment of radiological casualties: current concept. Ann Emerg Med. Jun. 2005;45(6):643-52.
Kohn et al., Protective effect of a recombinant amino-terminal fragment of bactericidal/permeability-increasing protein in experimental endotoxemia. J Infect Dis. Nov. 1993;168(5):1307-10.
Konchalovsky et al., Multiple organ involvement and failure: selected Russian radiation accident cases re-visited. BJR Suppl. 2005;27:26-9.
Levin et al., Recombinant bactericidal/permeability-increasing protein (rBPI21) as adjunctive treatment for children with severe meningococcal sepsis: a randomised trial. rBPI21 Meningococcal Sepsis Study Group. Lancet. Sep. 16, 2000;356(9234):961-7.
Levy et al., Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. J Immunol. Oct. 1, 2004;173(7):4627-34.
Marshall et al., Measurement of endotoxin activity in critically ill patients using whole blood neutrophil dependent chemiluminescence. Crit Care. Aug. 2002;6(4):342-8. Epub May 2, 2002.
Marsik et al., Endotoxaemia modulates Toll-like receptors on leucocytes in humans. Br J Haematol. May 2003;121(4):653-6.
Matsuzawa, Survival time in germfree mice after lethal whole body x-irradiation. Tohoku J Exp Med. Apr. 25, 1965;85:257-63.
McLaughlin et al., Effects of the germfree state on responses of mice to whole-body irradiation. Radiat Res. Nov. 1964;23:333-49.
Miller et al., The role of infection in radiation injury. Trans Assoc Am Physicians. 1950;63:155-60.
Munford, Sensing gram-negative bacterial lipopolysaccharides: a human disease determinant? Infect Immun. Feb. 2008;76(2):454-65. Epub Dec. 17, 2007.
Nathe et al., Endotoxin-directed innate immunity in tracheal aspirates of mechanically ventilated human neonates. Pediatr Res. Aug. 2009;66(2):191-6. doi: 10.1203/PDR.0b013e3181aa33d7.
Onoue et al., Effect of intestinal microflora on the survival time of mice exposed to lethal whole-body gamma irradiation. Radiat Res. Dec. 1981;88(3):533-41.
Ooi et al., Endotoxin-neutralizing properties of the 25 kD N-terminal fragment and a newly isolated 30 kD C-terminal fragment of the 55-60 kD bactericidal/permeability-increasing protein of human neutrophils. J Exp Med. Sep. 1, 1991;174(3):649-55.
Packey et al., Microbial influences on the small intestinal response to radiation injury. Curr Opin Gastroenterol. Mar. 2010;26(2):88-94. doi: 10.1097/MOG.0b013e3283361927.
Palmer et al., Deficient expression of bactericidal /permeability-increasing protein in immunocompromised hosts: translational potential of replacement therapy. Biochem Soc Transac. Aug. 2011 (Aug. 2011); 39(4):994-999. XP002727159.
Parikh et al., Excess Circulating Angiopoietin-2 May Contribute to Pulmonary Vascular Leak in Sepsis in Humans. PloS Medicine. Mar. 2006;3(3):0356-70.
Philipson et al., Treatment of post-irradiation infections in mice. III. Studies on the endogenous bacteraemia associated with ionizing radiation. Acta Pathol Microbiol Scand. 1958;43(1):62-72.
Quarmby et al., Radiation-induced normal tissue injury: role of adhesion molecules in leukocyte-endothelial cell interactions. Int J Cancer. Jul. 30, 1999;82(3):385-95.
Roses et al., Radiation therapy and Toll-like receptor signaling: implications for the treatment of cancer. Oncogene. Jan. 7, 2008;27(2):200-7. doi: 10.1038/sj.onc.1210909.
Schaad, Fluoroquinolone antibiotics in infants and children. Infect Dis Clin North Am. Sep. 2005;19(3):617-28.
Shalit et al., Enhanced hematopoiesis in sublethally irradiated mice treated with various quinolones. Eur J Haematol. Feb. 1997;58(2):92-8.
Stone et al., Models for evaluating agents intended for the prophylaxis, mitigation and treatment of radiation injuries. Report of an NCI Workshop, Dec. 3-4, 2003. Radiat Res. Dec. 2004;162(6):711-28.
Thomas et al., Bone-marrow transplantation (second of two parts). N Engl J Med. Apr. 24, 1975;292(17):895-902.
Thornley et al., A multiagent strategy to decrease regimen-related toxicity in children undergoing allogeneic hematopoietic stem cell transplantation. Biol Blood Marrow Transplant. Sep. 2004;10(9):635-44.

(56) References Cited

OTHER PUBLICATIONS

Van Der Schaft et al., Bactericidal/permeability-increasing protein (BPI) inhibits angiogenesis via induction of apoptosis in vascular endothelial cells. Blood. Jul. 1, 2000;96(1):176-81.

Van Der Velden et al., Intestinal damage determines the inflammatory response and early complications in patients receiving conditioning for a stem cell transplantation. PLoS One. Dec. 20, 2010;5(12):e15156. doi: 10.1371/journal.pone.0015156.

Vijay-Kumar et al., Flagellin treatment protects against chemicals, bacteria, viruses, and radiation. J Immunol. Jun. 15, 2008;180(12):8280-5.

Von Der Möhlen et al., Inhibition of endotoxin-induced activation of the coagulation and fibrinolytic pathways using a recombinant endotoxin-binding protein (rBPI23). Blood. Jun. 15, 1995;85(12):3437-43.

Von Der Möhlen et al., Inhibition of endotoxin-induced cytokine release and neutrophil activation in humans by use of recombinant bactericidal/permeability-increasing protein. J Infect Dis. Jul. 1995;172(1):144-51.

Wang et al., Total body irradiation selectively induces murine hematopoietic stem cell senescence. Blood. Jan. 1, 2006;107(1):358-66. Epub Sep. 8, 2005.

Waselenko et al., Medical management of the acute radiation syndrome: recommendations of the Strategic National Stockpile Radiation Working Group. Ann. Intern Med. Jun. 15, 2004;140(12):1037-51.

Wiezer et al., Bactericidal/permeability-increasing protein preserves leukocyte functions after major liver resection. Ann Surg. Aug. 2000;232(2):208-15.

Wiezer et al., Pharmacokinetics of a recombinant amino terminal fragment of bactericidal/permeability increasing protein (rBPI21) after liver surgery in rats and humans. Shock. Sep. 1998;10(3):161-6.

Zhang et al., Acute alcohol intoxication inhibits the lineage-c-kit+ Sca-1+ cell response to *Escherichia coli* bacteremia. J Immunol. Feb. 1, 2009;182(3):1568-76.

C.
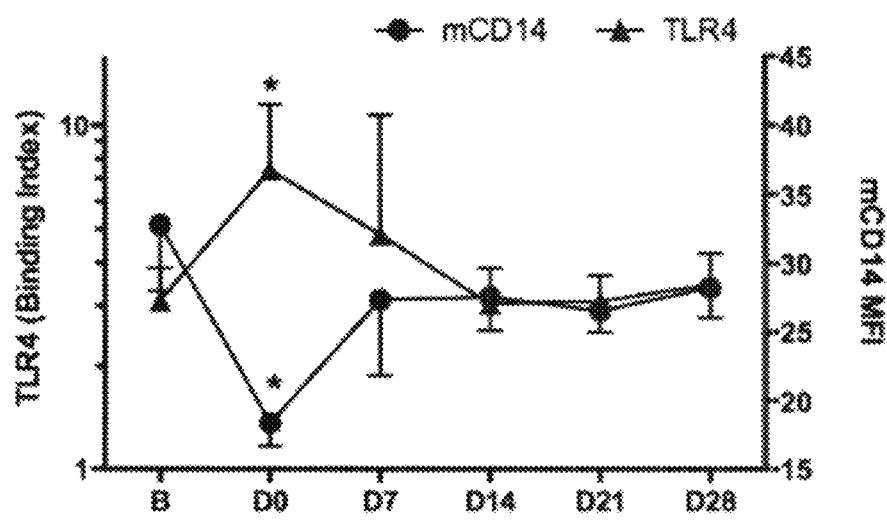
D.
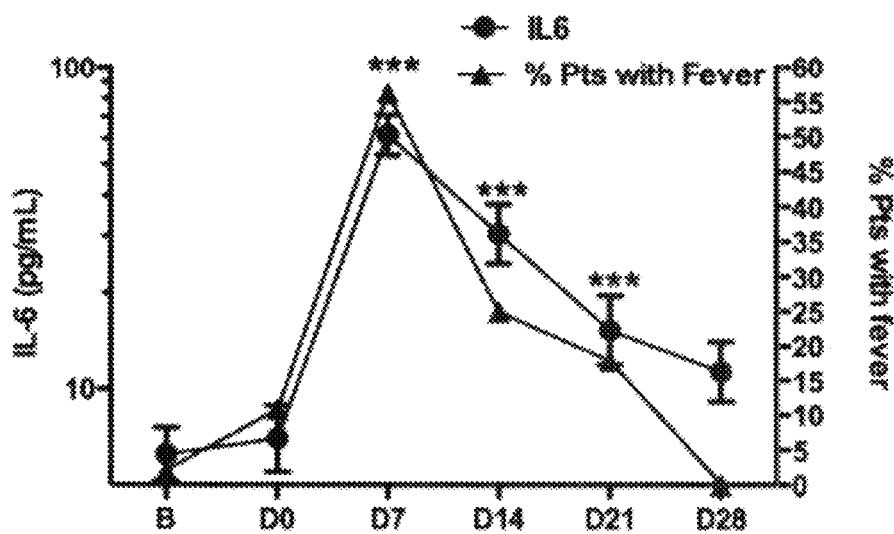
Fig. 1

Fig. 2
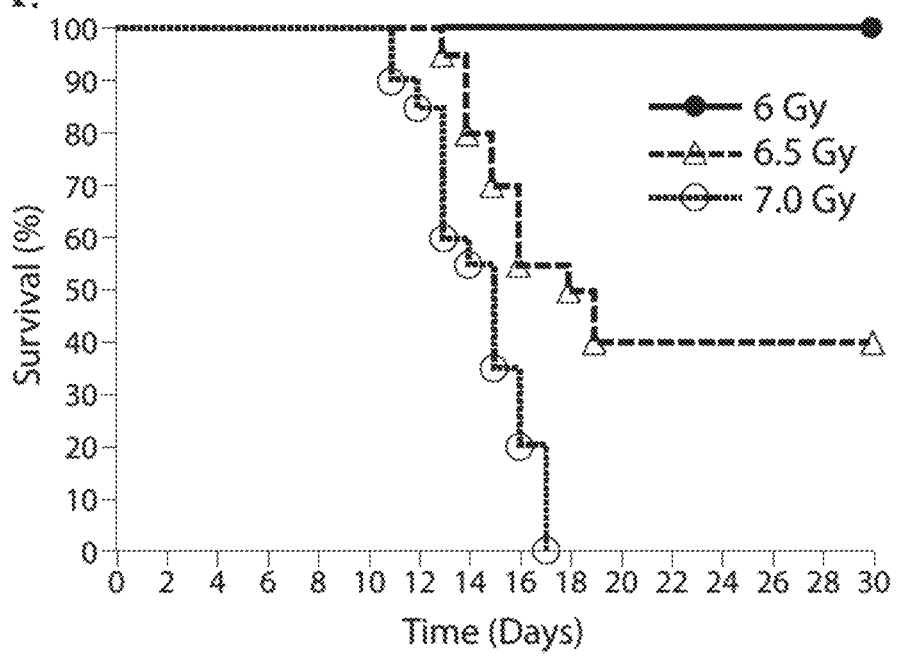
A.
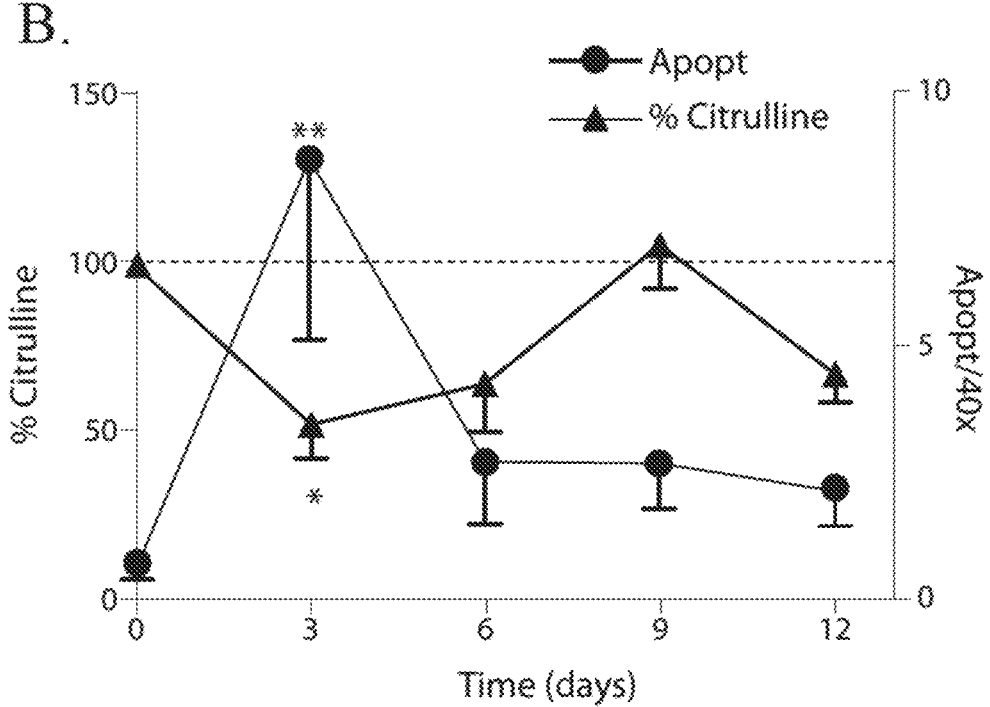
B.

Fig. 2
C.
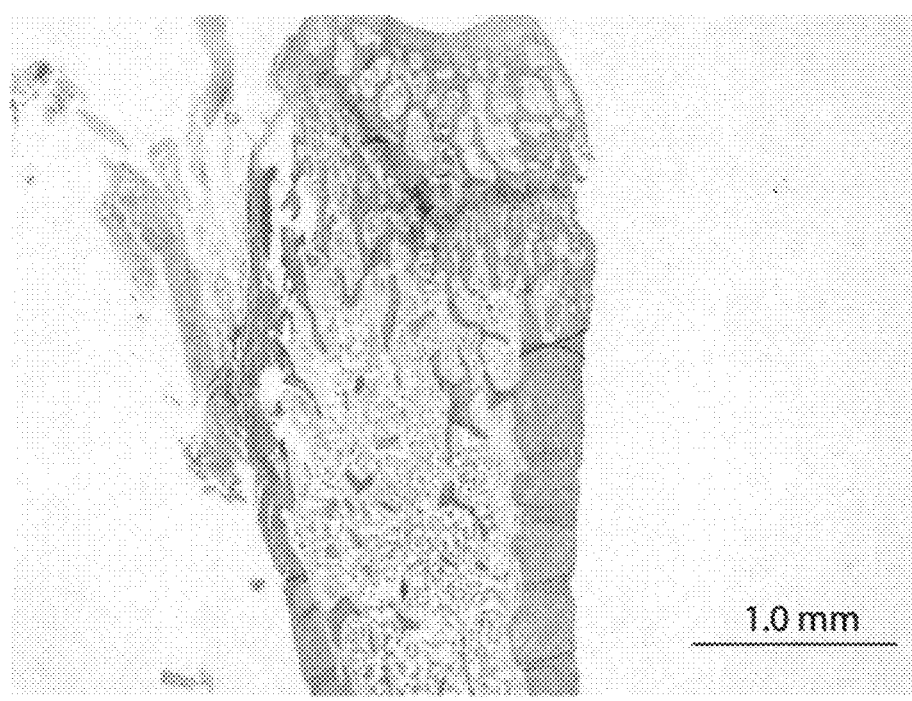
D.
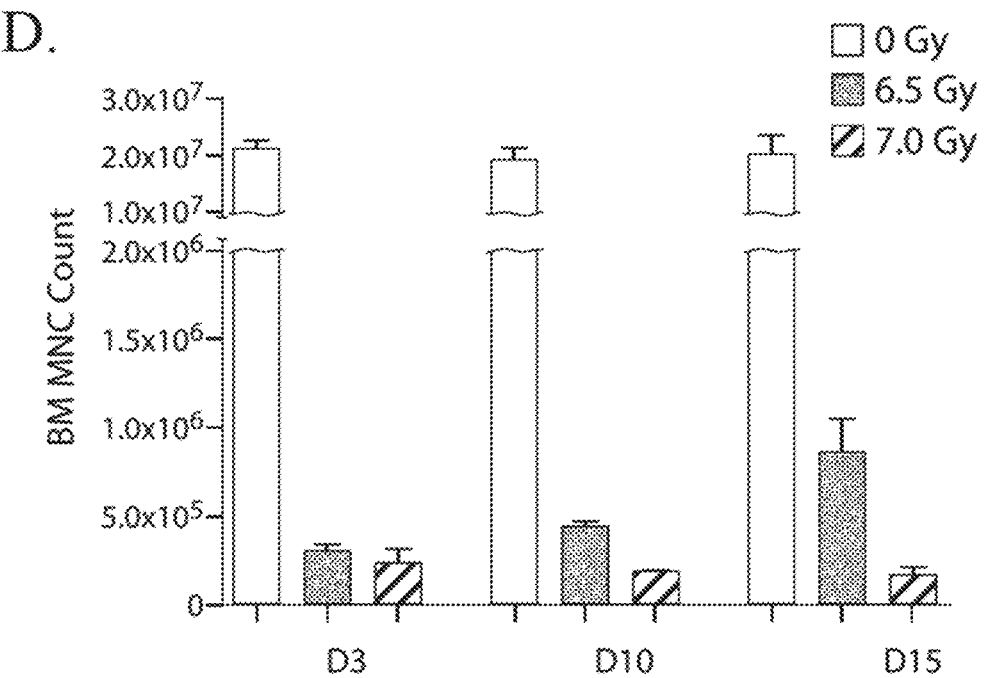

Fig. 2
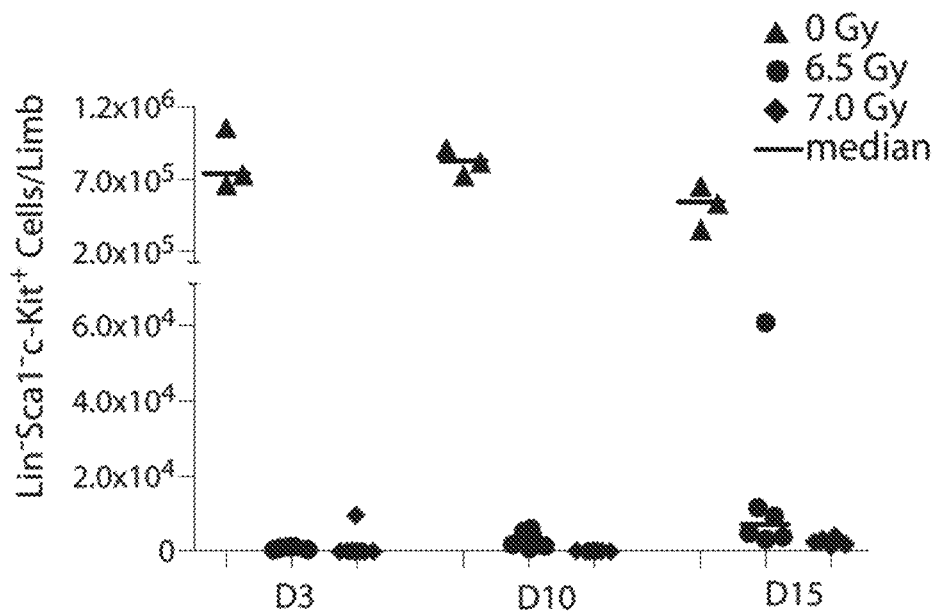
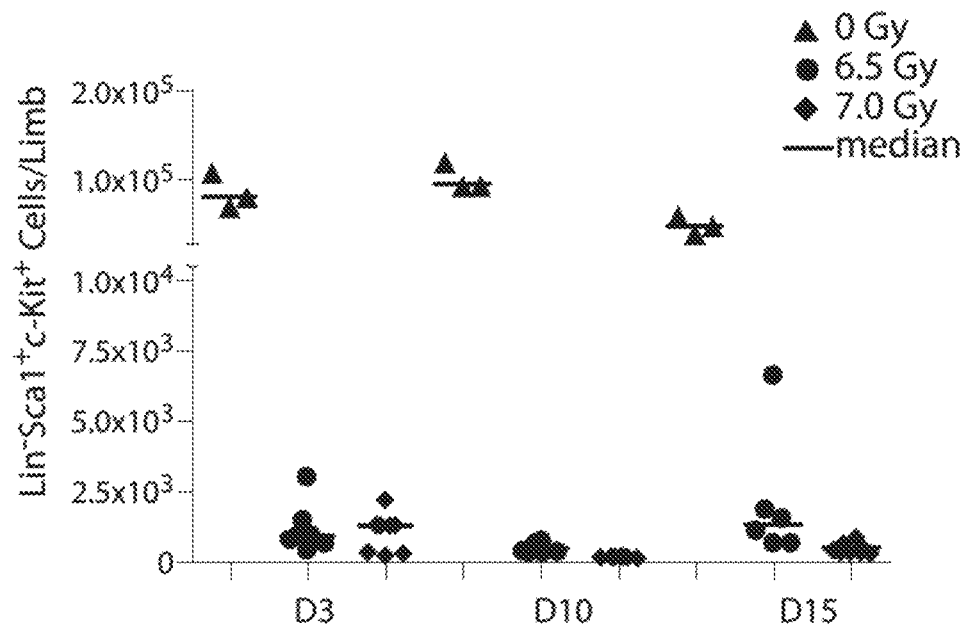

Fig. 4
A.
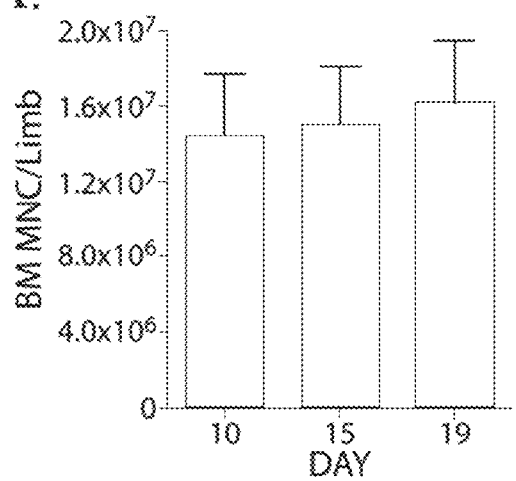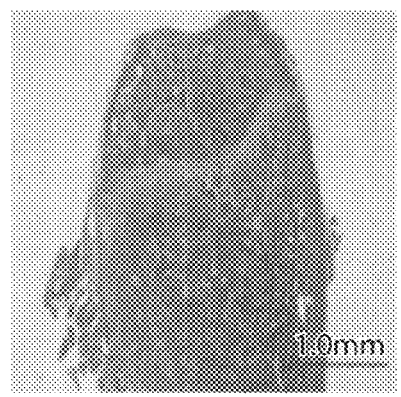
B.
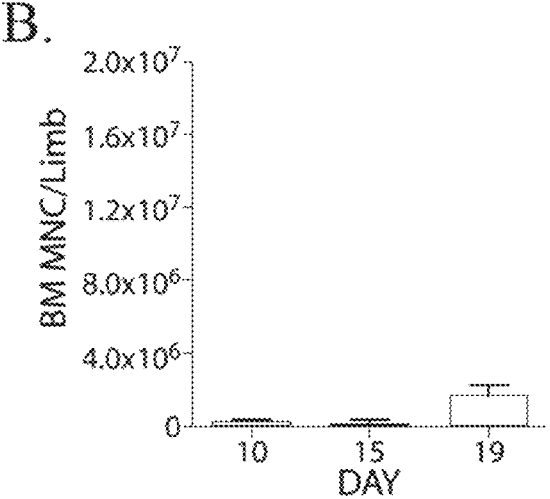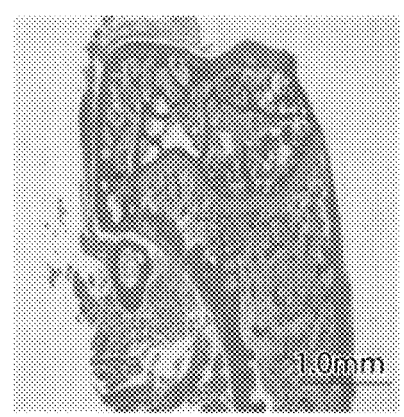
C.
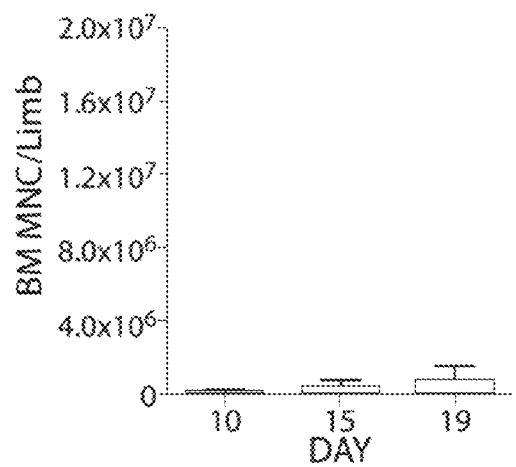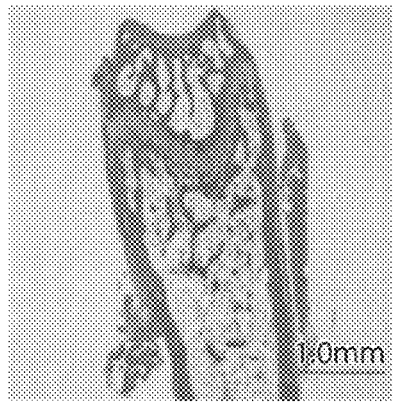

Fig. 4
D.
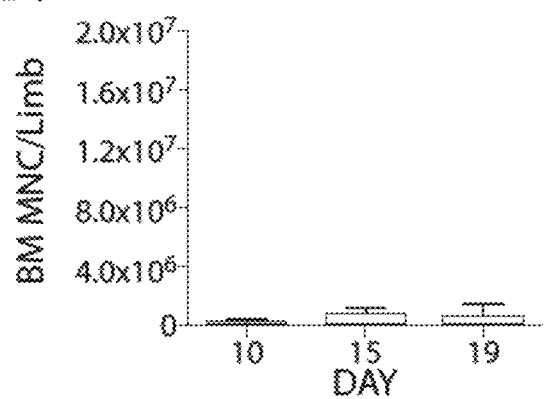 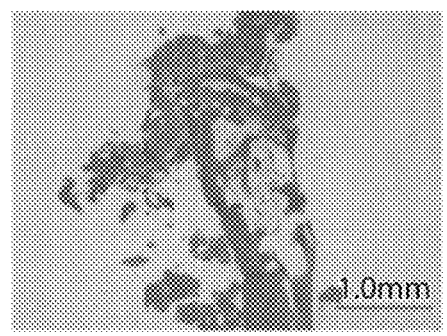
E.
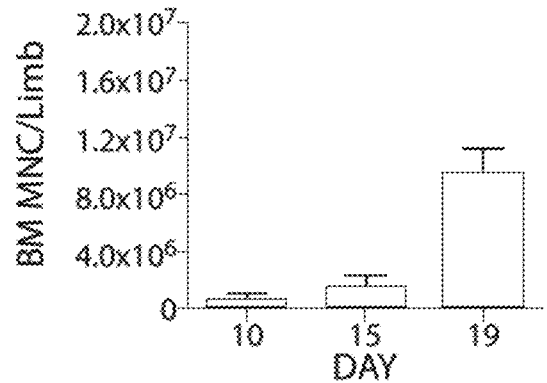 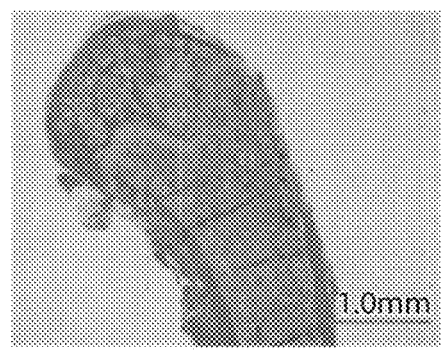

Fig. 14
A.
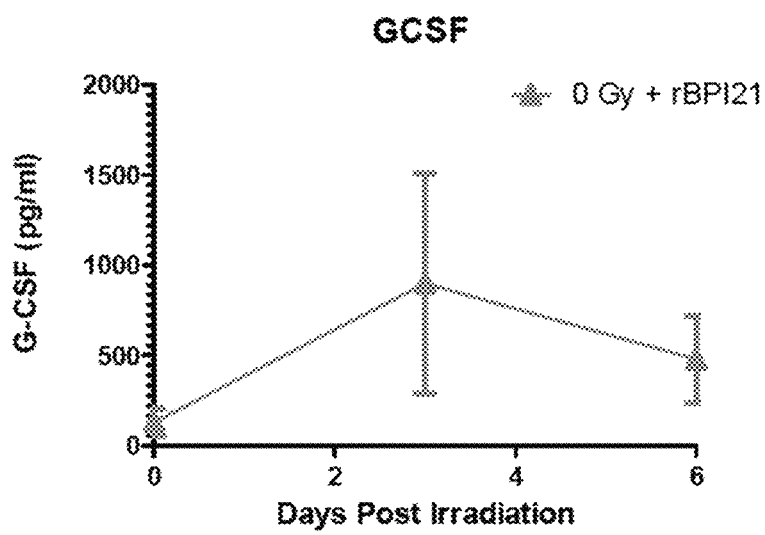
B. The above data in 0 Gy in related to 7 Gy mice
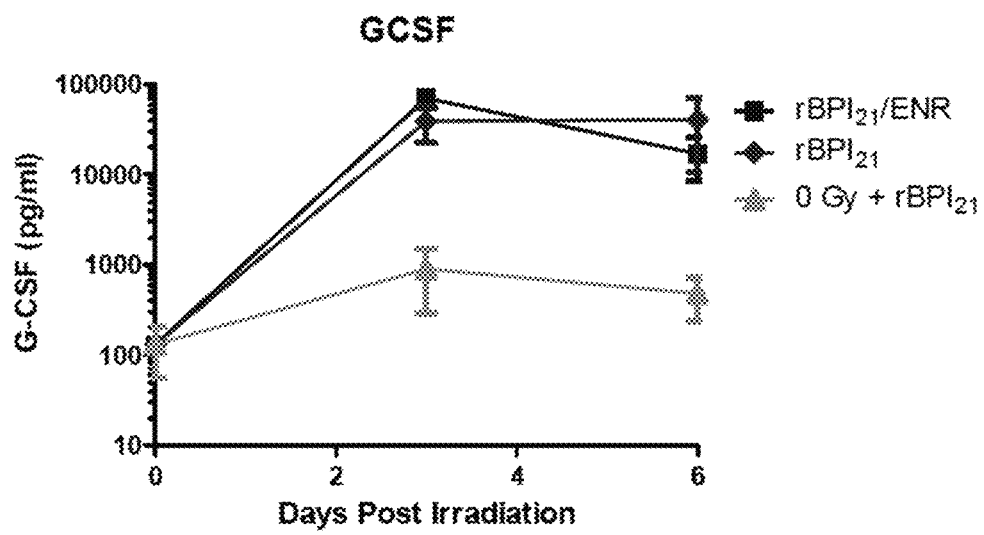

Fig. 14
C.
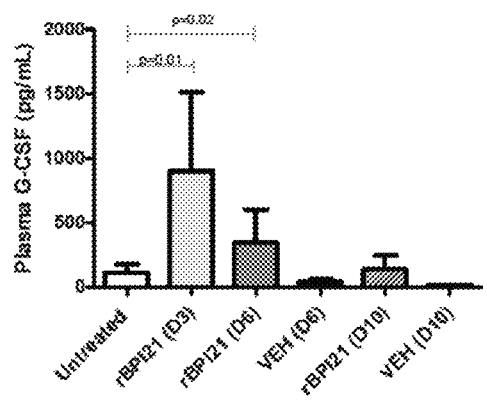
D.  E.
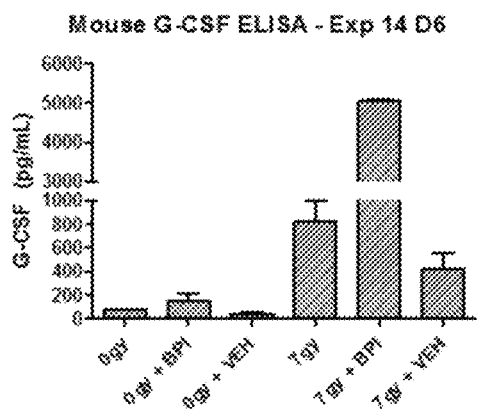 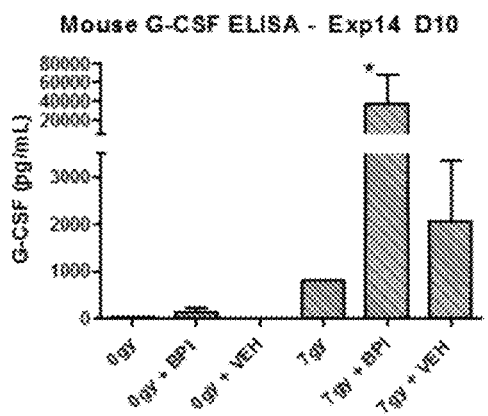
* Estimate - 1 value out of range
0 Gy mice injected 2x per day

BPI AND ITS CONGENERS AS RADIATION MITIGATORS AND RADIATION PROTECTORS

RELATED APPLICATIONS

This application is a divisional of Ser. No. 14/009,201, filed Oct. 1, 2013, which is a national stage filing under 35 U.S.C. §371 of international application PCT/US2012/032288, filed Apr. 5, 2012, which was published under PCT Article 21(2) in English, and claims the benefit under 35 U.S.C. §119(e) of U.S. provisional application Ser. No. 61/471,896, filed Apr. 5, 2011 the disclosures of which are incorporated by reference herein in their entireties.

GOVERNMENT SUPPORT

This invention was made with government support under grant numbers U19 AI067751 awarded by The National Institutes of Health and HR0011-08-1-0011 awarded by The Defense Advanced Research Projects Agency. The government has certain rights in the invention.

BACKGROUND OF THE INVENTION

Exposure of humans to radiation can cause serious harm, even death. Exposure can be accidental, resulting, for example, from a radiation leak at a nuclear power plant. Exposure also can be intentional, resulting, for example, from an act of terror. The most common circumstance of radiation exposure results from medical interventions, such as for the treatment of cancer. Radiation in this context can be local or systemic. When applied locally, radiation can nonetheless cause unwanted injury to healthy tissue in the pathway of the radiation. When applied systemically (i.e., total body irradiation), low doses can lead to bone marrow damage and gastrointestinal tract toxicity. High doses of total body irradiation can lead to permanent bone marrow damage, gut and lung toxicity, and sometimes death. There is a need for effective treatments which protect healthy tissues and mitigate the acute and chronic effects of exposure to ionizing radiation.

SUMMARY OF THE INVENTION

Described herein is a method of mitigating, in a subject (individual), tissue injury resulting from exposure to radiation (accidental/unintentional or intentional, such as therapeutic), chemoradiotherapy or disease. The method comprises administering to the subject (individual), referred to as a subject in need thereof, bactericidal/permeability increasing protein (BPI), a (at least one, one or more) BPI congener or both BPI and a BPI congener in an amount sufficient to reduce (partially or completely) the effects of exposure, thereby mitigating tissue injury resulting from radiation exposure in the subject. In certain embodiments, the radiation exposure results from accidental exposure to radiation, such as occurs in the event of a nuclear plant failure, or intentional exposure to radiation, such as therapeutic radiation, chemoradiotherapy or radiotherapy. Tissue injury can be, for example, injury to hematopoietic tissue (e.g., bone marrow) or injury to the gastrointestinal (GI) tract. In a particular embodiment, the tissue injury is hematopoietic toxicity. BPI congeners used in the method include, but are not limited to, $rBPI_{21}$, $rBPI_{23}$, $rBPI_{50}$, $rBPI(10-193)ala^{132}$ and a N-terminal fragment of BPI having an approximate molecular weight of from about 20 kD to about 25 kD.

In certain embodiments, BPI and/or its congeners is administered between 1 day before exposure of the subject to radiation and 2 days (48 hours) after exposure of the subject to the radiation. BPI and/or its congeners can be administered orally, intravenously, or subcutaneously.

In some embodiments, the method of mitigating tissue injury in a subject resulting from exposure to radiation (accidental/unintentional or intentional, such as therapeutic), chemoradiotherapy or disease further comprises administering an (at least one, one or more) antibiotic to the subject (a subject in need thereof). The antibiotic can be, for example, a quinolone antibiotic, such as an antibiotic selected from the group consisting of moxifloxacin, ciprofloxacin, levofloxacin, garenoxacin and delafloxacin.

In another aspect, the method is a method of mitigating hematopoietic toxicity in a subject (individual) resulting from exposure to radiation (accidental/unintentional or intentional, such as therapeutic), chemoradiotherapy, disease, toxin or drug or biologic mediated therapy. The method comprises administering to the subject (individual), referred to as a subject in need thereof, bactericidal/permeability increasing protein (BPI), a (at least one, one or more) BPI congener or both BPI and a BPI congener in an amount sufficient to mitigate (partially or completely) the hematopoietic toxicity of the subject. BPI congeners used in the method include, but are not limited to, $rBPI_{21}$, $rBPI_{23}$, $rBPI_{50}$, $rBPI(10-193)ala^{132}$ and a N-terminal fragment of BPI having an approximate molecular weight of from about 20 kD to about 25 kD.

In certain embodiments, BPI and/or its congeners is administered between 1 day before exposure of the subject to radiation and 2 days (48 hours) after exposure of the subject to the radiation. BPI and/or its congeners can be administered orally, intravenously, or subcutaneously.

In some embodiments, the method of mitigating hematopoietic toxicity in a subject (individual) resulting from exposure to radiation (accidental/unintentional or intentional, such as therapeutic), chemoradiotherapy, disease, toxin, or drug or biologic mediated therapy further comprises administering an (at least one, one or more) antibiotic to the subject (a subject in need thereof). The antibiotic can be, for example, a quinolone antibiotic, such as an antibiotic selected from the group consisting of moxifloxacin, ciprofloxacin, levofloxacin, garenoxacin and delafloxacin.

A further embodiment is a method for bone marrow recovery in a subject (individual), the method comprising: administering to the subject (individual), referred to as a subject in need thereof, bactericidal/permeability increasing protein (BPI), a (at least one, one or more) BPI congener or both BPI and a BPI congener in an amount sufficient for bone marrow recovery in the subject. BPI congeners used in the method include, but are not limited to, $rBPI_{21}$, $rBPI_{23}$, $rBPI_{50}$, $rBPI(10-193)ala^{132}$ and a N-terminal fragment of BPI having an approximate molecular weight of from about 20 kD to about 25 kD.

In certain embodiments, BPI and/or its congeners is administered between 1 day before exposure of the subject to radiation and 2 days (48 hours) after exposure of the subject to the radiation. BPI and/or its congeners can be administered orally, intravenously, or subcutaneously.

In certain embodiments, the subject has a deficiency in one or more hematopoietic cell types or lineages. For example, a subject may have a hematopoietic deficiency such as lymphopenia, myelopenia, leukopenia, neutropenia, erythropenia, megakaryopenia, a deficiency in platelets, a deficiency in monocytes, a deficiency in lymphocytes, a deficiency in erythrocytes, deficiency in neutrophils, a deficiency in T cells, a deficiency in granulocytes, and/or a deficiency in dendritic cells. The deficiency in one or more hematopoietic cell types or lineages may result from exposure to radiation, chemoradiotherapy, radiotherapy, disease, toxin, or drug or biologic mediated therapy.

In some embodiments, the method of bone marrow recovery in a subject (individual) resulting from exposure to radiation (accidental/unintentional or intentional, such as therapeutic), chemoradiotherapy, disease, toxin or drug or biologic mediated therapy further comprises administering an (at least one, one or more) antibiotic to the subject (a subject in need thereof). The antibiotic can be, for example, a quinolone antibiotic, such as an antibiotic selected from the group consisting of moxifloxacin, ciprofloxacin, levofloxacin, garenoxacin and delafloxacin.

A further embodiment is a method for stimulating hematopoiesis in a subject (individual), the method comprising: administering to the subject (individual), referred to as a subject in need thereof, bactericidal/permeability increasing protein (BPI), a (at least one, one or more) BPI congener or both BPI and a BPI congener in an amount sufficient to stimulate hematopoiesis in the subject. BPI congeners used in the method include, but are not limited to, $rBPI_{21}$, $rBPI_{23}$, $rBPI_{50}$, $rBPI(10-193)ala^{132}$ and a N-terminal fragment of BPI having an approximate molecular weight of from about 20 kD to about 25 kD.

In certain embodiments, the subject has a deficiency in one or more hematopoietic cell types or lineages. The hematopoietic deficiency can be, for example, lymphopenia, myelopenia, leukopenia, neutropenia, erythropenia, megakaryopenia, a deficiency in platelets, a deficiency in monocytes, a deficiency in lymphocytes, a deficiency in erythrocytes, a deficiency in neutrophils, a deficiency in T cells, a deficiency in granulocytes, and/or a deficiency in dendritic cells. The deficiency in one or more hematopoietic cell types or lineages results, for example, from exposure to radiation, chemoradiotherapy, radiotherapy, disease, toxin or drug or biologic mediated therapy. BPI congeners used in the method include, but are not limited to, $rBPI_{21}$, $rBPI_{23}$, $rBPI_{50}$, $rBPI(10-193)ala^{132}$ and a N-terminal fragment of BPI having an approximate molecular weight of from about 20 kD to about 25 kD.

In certain embodiments, BPI and/or its congeners is administered between 1 day before exposure of the subject to radiation and 2 days (48 hours) after exposure of the subject to the radiation. BPI and/or its congeners can be administered orally, intravenously, or subcutaneously.

In certain embodiments, the method for stimulating hematopoiesis in a subject (individual) further comprises administering an (at least one, one or more) antibiotic to the subject (a subject in need thereof). The antibiotic can be, for example, a quinolone antibiotic, such as an antibiotic selected from the group consisting of moxifloxacin, ciprofloxacin, levofloxacin, garenoxacin and delafloxacin.

As described herein, in certain embodiments, the method comprises administering (a) bactericidal/permeability increasing protein (BPI), a (at least one, one or more) BPI congener or both BPI and a BPI congener and (b) an (at least one, one or more) antibiotic to a subject (individual) in need thereof. In those embodiments, the bactericidal/permeability increasing protein (BPI), BPI congener or both BPI and a BPI congener and the antibiotic can be administered simultaneously (together) or sequentially. In those instances in which the bactericidal/permeability increasing protein (BPI), BPI congener or both BPI and a BPI congener and the antibiotic are administered simultaneously, they can be administered in one composition or in separate compositions. In those instances in which the bactericidal/permeability increasing protein (BPI), BPI congener or both BPI and a BPI congener and the antibiotic are administered sequentially, they can be administered in either order and need to be administered sufficiently close in time that they have the desired mitigating effect.

The subject (individual) is an animal, typically a mammal. In one aspect, the subject is a dog, a cat, a horse, a sheep, a goat, a cow or a rodent. In important embodiments, the subject is a human. In any of the foregoing embodiments, the subject is not otherwise in need of treatment with BPI and/or its congeners. In some such embodiments, the subject does not have an infectious disease.

These and other aspects of the inventions, as well as various advantages and utilities will be apparent with reference to the Detailed Description. Each aspect of the invention can encompass various embodiments as will be understood.

BRIEF DESCRIPTION OF THE DRAWINGS

FIG. 2. BALB/c mice exhibit BM ablation and mortality at 7 Gy. (A) D30 mortality after 6 (n=10), 6.5 (n=20) and 7 (n=20) Gy TBI differed by dose (p<0.001, Mantel-Cox log-rank). (B) Rapid onset of mucosal damage was documented by peak colonic epithelial apoptosis at D3 (n=5) post-TBI, coincident with nadir in plasma citrulline levels (n=7), depicted normalized to levels before TBI (D0=100%). Data represent means±SEM. *p<0.05 analyzed by 1-sample t test compared to D0; **p<0.001 by Mann-Whitney. (C) Representative H&E stained femur section demonstrates BM ablation D3 after 7 Gy TBI (4× magnification). (D) BM MNC counted after 0 Gy (normal controls, n=3/timepoint), 6.5 Gy (n=8/timepoint), and 7 Gy (n=8 on days 3 and 10, n=6 on D15 due to greater mortality). Data are the mean±SD of individual counts. Fewer BM MNC were present after 7 vs 6.5 Gy (D3 p=0.05, D10 p=0.0002, D15 p=0.02) Flow cytometry analysis of LK (E), and LSK cells (F) in BM of the same mice indicated 7 Gy produced prolonged reduction in progenitor and HSC numbers. By D15, 6.5 mice had greater LK and LSK cell numbers than 7 Gy mice (p=0.01 for both LK and LSK). Each symbol represents the absolute LK or LSK number within BM from one limb of an individual animal. Median values/group are indicated by horizontal bars. Hematologic data analyzed by Mann-Whitney.

FIG. 4. $rBPI_{21}$/ENR accelerates hematopoietic recovery after TBI-induced aplasia. BALB/c BM MNC count (of one hind limb) and histopathology (from the contralateral hind limb) were assessed 10, 15, and 19 days after various treatments. Data shown for (A) untreated, age-matched controls (normals) or (b) 7 Gy irradiated mice. Other mice received both 7 Gy TBI and the following treatments started 24 hrs after irradiation: (C) ENR, (D) VEH/ENR or (E) $rBPI_{21}$/ENR. Left panels: Each graph shows counts (mean±SD) of BM MNC flushed from a hind leg of 8 individual mice/group except (B) where the high mortality (median survival 12-15 days) experienced by mice given 7 Gy alone resulted in n=2-8/timepoint. The $rBPI_{21}$/ENR combination resulted in improved BM cellularity as compared to 7Gy, ENR and VEH/ENR on D10 (p=0.0003, 0.001 and <0.0001, respectively), D15 (p=0.0007, p=0.001 and p=0.001, respectively) and D19 (p=0.0006, p<0.0001 and p<0.0001, respectively) by Mann-Whitney. Data are aggregated from two replicate studies. Similar results were obtained in both studies. Right panels: Representative D19 H&E stained sections of the femurs of animals receiving indicated treatments demonstrate the close correlation of BM MNC counts with BM histology.

DETAILED DESCRIPTION OF THE INVENTION

Figure 1:
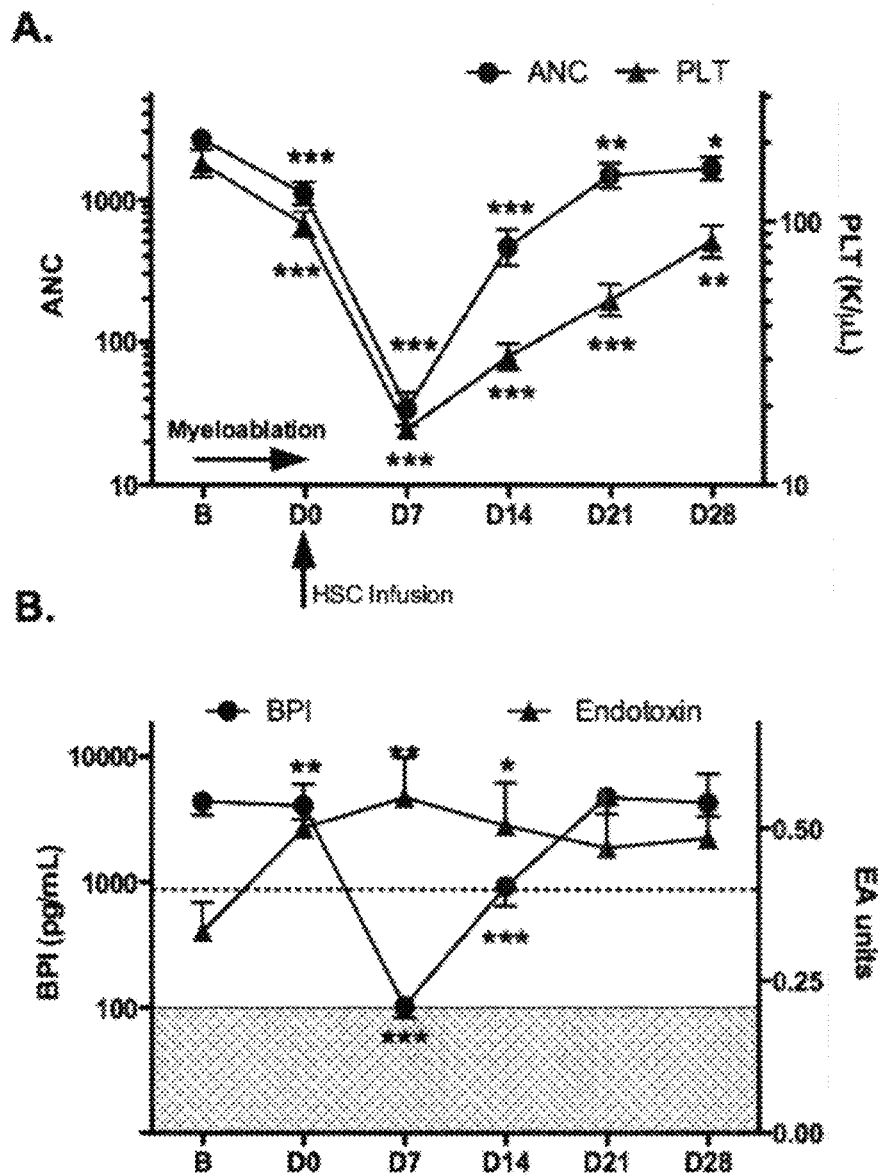
FIG. 1. Changes in circulating levels of neutrophils (ANC) and platelets (PLT), monocyte surface levels of mCD14 and TLR4, plasma levels of endotoxin, BPI, and IL-6, and incidence of fever are observed after human myeloablative HSCT. (A) Severe neutropenia (n=46) and thrombocytopenia occurred (n=48, nadir D7). Data represent geometric means+SEM of log transformed values labeled in original units. (B) Plasma endotoxin was evaluated in 18 patients by endotoxin activity assay (EAA) and reported in EAA units at baseline (B; n=17) and for D0 (n=17), D7 (n=10), D14 (n=15), D21 (n=15) and D28 (n=3) after myeloablation. The horizontal dashed line (at 0.4 EA units) indicates lower limit of detection (LLD). Plasma BPI concentrations in pg/mL were assessed by ELISA at B (n=48), D0 (n=46), D7 (n=48), D14 (n=48), D21 (n=47) and D28 (n=33). The dotted line indicates the LLD for BPI ELISA (<100 pg/ml). Samples which fell below the LLD were assigned a value of 50% the LLD. (C) Measurement of monocyte mCD14 and TLR4 surface expression by flow cytometry revealed a nadir for mCD14 at D0 (n=10) and concurrent peak TLR4 expression at D0 (n=9). Data represent mean fluorescence intensity (mCD14) or binding index (TLR4) geometric means+SEM of log transformed values labeled in original units. (D) Plasma IL-6 (n=37) and fever incidence (n=48) both peaked on D7. IL-6 data represent geometric means+SEM of log transformed values labeled in original units.

The present invention, in one aspect, relates to the surprising discovery that bactericidal/permeability increasing protein (BPI) and/or its congeners, alone or in combination with an antibiotic, can mitigate tissue injury resulting from exposure to radiation, chemotherapy, or disease. As described herein, BPI and/or its congeners, alone or in combination with an antibiotic, can be used to mitigate hematopoietic toxicity, stimulate hematologic function and aid bone marrow recovery in subjects (individuals) exposed to accidental or incidental radiation, and/or in subjects with severe myeloblation, involving depletion/failure of bone marrow cells.

As used herein, a subject in need of BPI and/or its congeners therapy, is a subject having a decrease (partial or complete) in bone marrow function. In some embodiments, the subject has insufficient hematopoiesis in one or more blood cell types or blood lineages. In some embodiments, the subject is exposed to radiation, chemoradiotherapy or a toxin, or has a disease, or a drug or biologic-mediated hematopoietic injury that results in a decrease (partial or complete) in bone marrow function in the subject. Examples of diseases that cause a decrease (partial or complete) in bone marrow function include, but are not limited to acute and chronic inflammation, infection, aplastic anemia, Fanconi anemia, Bloom syndrome, reticular dysgenesis, Kostmann syndrome, congenital benign neutropenia, neonatal sepsis, myelodysplastic syndrome, Diamond-Blackfan anemia and congenital or acquired marrow failure syndrome. The subject is not otherwise in need of treatment with BPI and/or its congeners. In some such embodiments, the subject does not have an infectious disease.

In some embodiments, the subject is exposed to levels of radiation sufficient to cause unwanted tissue injury and/or hematopoietic toxicity. In some embodiments, the subject has been exposed to—radiation sufficient to cause tissue injury and/or hematopoietic toxicity prior to BPI and/or its congeners therapy. In some embodiments, the subject has not been exposed to radiation and prior to exposure radiation sufficient to cause tissue injury and/or hematopoietic toxicity receives treatment with BPI and/or its congeners in anticipation of future radiation exposure. In some embodiments, the subject is being exposed to radiation during BPI and/or its congeners therapy. Radiation exposure includes, but is not limited to, accidental exposure, exposure resulting from a nuclear attack, and medical radiation therapy such as local therapy and low and high dose total body irradiation. In some embodiments, the subject has cancer, and has undergone, is undergoing or will undergo radiation therapy, chemoradiotherapy and/or chemotherapy.

According to some aspects of the invention, a method for mitigating radiation-induced tissue injury of any type is provided. Exposure to radiation is toxic at low doses and life threatening at high doses. The tissues which are most vulnerable to radiation-induced damage include the hematopoietic system and the gastrointestinal tract (GI). Moderate doses of radiation can cause a rapid reduction in blood cells counts, including loss of circulating lymphocytes and a reduction in mitotically active hematopoietic progenitor cells. Reduction in blood cell count is associated, among other things, with increased risk of infections, and cancer development. Higher doses of radiation can lead to more severe and often permanent bone marrow damage, resulting from loss of bone marrow stem cell populations. Thus, the tissue injury may be, for example, a decrease in blood cell count, loss of bone marrow stem cell populations, or hematopoietic toxicity.

According to some aspects of the invention, a method for mitigating hematopoietic toxicity is provided. The method comprises administering BPI and/or its congeners, alone or in combination with an antibiotic. The term 'hematopoietic toxicity' refers to a toxicity that substantially arises from exposure to radiation that adversely affects the hematopoietic system of an individual (subject). Alternatively, hematopoietic toxicity may result from exposure of the subject to a toxin or a disease or a genetic predisposition to hematopoietic injury. This adverse effect can be manifested in the subject broadly, in that the levels of many hematopoietic cell types are altered (differ from levels considered to be normal), as a result of the radiation exposure, chemotherapy, toxin or disease, or the adverse effect can be manifested in the subject more specifically, in that only one or a few hematopoietic cell types differ from levels considered to be normal as a result of the exposure to the radiation, chemotherapy, toxin or disease.

BPI and/or its congeners and antibiotic(s) are administered for mitigating tissue injury, such as hematopoietic toxicity. As used herein, the term "mitigate" refers to a reduction in the extent of disease, chemotherapy, toxin or radiation-induced tissue damage (damage is less than would occur in the absence of BPI/congener treatment). As such, the reduction in the extent of disease, chemotherapy, toxin or radiation-induced tissue damage may be evaluated in terms of an improvement in the health of the tissue in treated subjects. An improvement in the health of tissues of treated subjects may be determined by examining the health of the tissue in treated subjects versus the health of tissue in control subjects (subjects receiving the same amount of radiation exposure treated subjects but not receiving the BPI therapy). The health of the tissue may be measured by any variety of methods known to those of ordinary skill in the art, including direct and indirect measurements. Direct measurements are those such as measuring cell count. In some embodiments, the tissue injury measured may be necrosis of the tissue, and/or a decrease in blood cell count. In some embodiments, the improvement in the health of the tissue may be measured by evaluating the function of the hematopoietic system using end points such as hematocrit, white blood cell count, incorporation of tritiated thymidine into bone marrow DNA, spleen weight, number of burst-forming units-erythroid or number of colony forming units (erythroid, granulocyte, macrophage and megakaryocyte forming lineages) from spleen or hone marrow obtained from humerus or femur or enumeration of circulating hematopoietic stem cells or other primitive hematopoietic cells in the peripheral circulation.

According to some aspects of the invention, a method for bone marrow recovery is provided. The method comprises administering BPI and/or its congeners, alone or in combination with an antibiotic. "Bone marrow recovery" means the process whereby bone marrow that has been damaged by radiation, chemotherapy, disease or toxins is restored to its normal or near normal state (function), or where a measurable improvement in bone marrow function is obtained. Bone marrow function is the process whereby the various blood cell types or lineages are produced from the hematopoietic (blood) stem cells. The end points that can be used to measure bone marrow recovery include, hut are not limited to hematocrit, white blood cell count, incorporation of tritiated thymidine into bone marrow DNA, spleen weight, number of burst-forming units-erythroid or number of colony forming units (erythroid, granulocyte, macrophage and megakaryocyte forming lineages) from spleen or bone marrow obtained from humerus or femur or enumeration of circulating hematopoietic stem cells or other primitive hematopoietic cells in the peripheral circulation. In some embodiments, the subject is exposed to radiation or a toxin, or has a disease, or a drug or biologic-mediated hematopoietic injury that results in a decrease (partial or complete) in bone marrow function in the subject. Examples of diseases that cause a decrease (partial or complete) in bone marrow function include, but are not limited to acute and chronic inflammation, infection, aplastic anemia, Fanconi syndrome, Bloom syndrome, reticular dysgenesis, Kostmann syndrome, congenital benign neutopenia, neonatal sepsis, myelodysplastic syndrome, Diamond-Blackfan anemia and congenital or acquired marrow failure syndrome.

According to some aspects of the invention, a method for stimulating hematopoiesis is provided. The method comprises administering BPI and/or its congeners, alone or in combination with an antibiotic. "Stimulation of hematopoiesis" generally refers to an increase in one or more hematopoietic cell types or lineages, and especially relates to a stimulation or enhancement of one or more hematopoietic cell types or lineages in cases where a subject has a deficiency in one or more hematopoietic cell types or lineages. The deficiency in one or more hematopoietic cell types or lineages may be caused by exposure to radiation or a toxin, a disease, drug or biologic-mediated hematopoietic injury. Examples of diseases that cause a deficiency in one or more hematopoietic cell types or lineages include, but are not limited to acute and chronic inflammation, infection, aplastic anemia, fanconi syndrome, Bloom syndrome, reticular dysgenesis, Kostmann syndrome, congenital benign neutopenia, neonatal sepsis, myelodysplastic syndrome, Diamond-Blackfan anemia and congenital or acquired marrow failure syndrome. Hematopoietic deficiency may comprise lymphopenia, leukopenia, neutropenia, erythropenia, megakaryocytopenia, a deficiency in platelets, a deficiency in monocytes, a deficiency in lymphocyctes, a deficiency in erythrocytes, deficiency in neutrophils, a deficiency in T cells, or B cells specifically, a deficiency in granulocytes, and/or a deficiency in dendritic cells.

The compounds useful in the methods of the invention are BPI, its biologically active fragments, analogs, variants and/or its congeners. BPI, a 50-55 kDa cationic antimicrobial protein found primarily in the azurophilic granules of human polymorphonuclear neutrophils, has the highest affinity (pM-nM) for a variety of bacteria-associated and cell-free forms of endotoxin. BPI binding to endotoxin promotes killing and clearance of Gram-negative bacteria and inhibits endotoxin-induced inflammation and apoptosis by precluding endotoxin binding to the cellular pro-inflammatory endotoxin receptor complex composed of mCD14, MD-2, and TLR4. Most BPI is intracellular but plasma levels of BPI rise with neutrophil activation and degranulation. Stable BPI congeners include, but are not limited to rBPI$_{21}$, rBPI$_{23}$, rBPI$_{50}$, rBPI(10-193)ala$^{132}$ and a N-terminal fragment of BPI having a molecular weight approximately between 20 to 25 kD. Preparation of BPI and its congeners has been have been described in the art in publications such as U.S. Pat. No. 6,268,345, U.S. Pat. No. 6,599,880, U.S. Pat. No. 5,420,019, U.S. Pat. No. 5,980,897 and US Pub No. 2008/0031874.

BPI and/or its congeners may be given in combination with an antibiotic (at least one, one or more antibiotic). In some embodiments, the antibiotic is a quinolone. In some embodiments, the quinolone is a fluoroquinolone, which has a fluorine atom attached to the central ring system, typically at position 6 or 7. Examples of quinolone antibiotics administered in combination with BPI and/or its congeners include, but are not limited to, moxifloxacin, ciprofloxacin, levofloxacin, garenoxacin, and delafloxacin.

BPI and/or its congeners and the antibiotic(s) may be administered simultaneously or sequentially. When BPI and/or its congeners and the antibiotic(s) are administered simultaneously, they can be administered in the same or separate formulation(s), and are administered at substantially the same time. The administration of the antibiotic(s) and BPI and/or its congeners may also be sequential; the two need only be administered sufficiently close in time to have the desired effect on bone marrow function. In certain embodiments, the antibiotic(s) are administered before BPI and/or its congeners or after the administration of BPI and/or its congeners. The separation in time between the administration of these compounds may be a matter of minutes, 5 hours, 12 hours, 24 hours, 48 hours, or 96 hours, or it may be longer.

The compounds of the present invention are administered in effective amounts. An effective amount is a dose sufficient to provide a medically desirable result and can be determined by one of skill in the art using routine methods. In the treatment of radiation-induced tissue damage, an effective amount will be that amount necessary to inhibit (partially or completely) tissue damage caused by exposure to radiation. In some embodiments, an effective amount is an amount which results in improvement in the condition being treated. In some embodiments, an effective amount may depend on the type and extent of radiation exposure, and/or the use of one or more additional therapeutic agents. However, one of skill in the art can determine appropriate doses and ranges of BPI/congener and antibiotic(s) to use, for example based on in vitro and/or in vivo testing and/or other knowledge of compound dosages. It should be appreciated that in some embodiments, BPI and/or its congeners and antibiotic(s) described herein may be administered in dosages that inhibit radiation-caused injury of non-cancerous tissues and cells, without materially interfering with the killing of cancerous tissues and cells.

When administered to a subject, effective amounts of BPI/congener and antibiotic(s) will depend on, for example, the severity of the injury; individual patient parameters including age, physical condition, size and weight, concurrent treatment, frequency of treatment, and the mode of administration. These factors are well known to those of ordinary skill in the art and can be addressed with no more than routine experimentation. In some embodiments, a maximum dose is used, that is, the highest safe dose according to sound medical judgment.

An effective amount typically will vary from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, from about 10.0 mg/kg to about 150 mg/kg in one or more dose administrations, for one or several or many days (depending on the mode of administration and the factors discussed above).

Actual dosage levels of the BPI/congener and antibiotic(s) can be varied to obtain an amount that is effective to achieve the desired therapeutic response for a particular patient, compositions, and mode of administration. The selected dosage level depends upon the activity of the particular compound, the route of administration, the severity of the radiation exposure, and prior medical history of the patient being treated. However, it is within the skill of the art to start treatment with doses of the compound at levels lower than required to achieve the desired therapeutic effort and to gradually increase the dosage until the desired effect is achieved.

BPI and/or its congeners and antibiotic(s) may be administered any time once the subject is diagnosed as having a decrease (partial or complete) in bone marrow function. In some embodiments, BPI and/or its congeners and antibiotic(s) is administered any time after the subject is diagnosed as having a decreased blood cell count as compared to expected normal levels. In some embodiments, BPI and/or its congeners and antibiotic(s) are administered before, during or after exposure of the subject to levels of radiation causing tissue damage. In some embodiments, BPI and/or its congeners and antibiotic(s) are administered before radiation exposure, but close enough in time to the radiation exposure to inhibit radiation-induced tissue damage. In some embodiments, BPI and/or its congeners and antibiotic(s) are administered any time up to 1 day before the radiation exposure. In some embodiments, BPI and/or its congeners and antibiotic(s) are administered between 1 and 24 hours before radiation exposure. In some embodiments, BPI and/or its congeners and antibiotic(s) are administered within 12 hours of radiation exposure. BPI and/or its congeners and antibiotic(s) may also be administered during radiation exposure. In some embodiments, BPI and/or its congeners and antibiotic(s) are administered after radiation exposure, yet close enough in time to the radiation exposure to have the desired effect of protecting tissue from radiation-induced tissue injury. In some embodiments, BPI and/or its congeners and antibiotic(s) is administered any time up to 3 days post-exposure. In some embodiments, BPI and/or its congeners and antibiotic(s) are administered between 1-60 hours following radiation exposure. In some embodiments, BPI and/or its congeners and antibiotic(s) are administered within 24 or 48 hours of radiation exposure. In some embodiments, the subject has cancer and the BPI and/or its congeners and antibiotic(s) are administered at least 1 hour, at least 12 hours, at least 24 hours, or at least 48 hours following radiation therapy, chemoradiotherapy, or chemotherapy, but not more than 72 hours following radiation therapy, chemoradiotherapy, or chemotherapy.

BPI and/or its congeners and antibiotic(s) and pharmaceutical compositions containing BPI and/or its congeners and antibiotic(s) are administered to a subject by any suitable route. For example, the compositions can be administered orally, including sublingually, rectally, parenterally, intracisternally, intravaginally, intraperitoneally, topically and transdermally (as by powders, ointments, or drops), bucally, or nasally. The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation also is contemplated, including, for example, embedding a composition of the invention in the body such as, for example, in the brain. In some embodiments, the compositions may be administered systemically.

Pharmaceutical compositions of the invention for parenteral injection comprise pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water ethanol, polyols (such as, glycerol, propylene glycol, polyethylene glycol, and the like), and suitable mixtures thereof, vegetable oils (such, as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions also can contain preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents such as sugars, sodium chloride, and the like. Prolonged absorption of the injectable pharmaceutical form can be brought about by the inclusion of agents which delay absorption, such as aluminum monostearate and gelatin.

In some cases, in order to prolong the effect of the drug, it is desirable to slow the absorption of the drug from a subcutaneous or intramuscular injection. This result can be accomplished by the use of a liquid suspension of amorphous materials with poor water solubility. Delayed absorption of a parenterally administered drug also is accomplished by dissolving or suspending the drug in an oil vehicle. Likewise, injectable depot forms are made by forming microencapsule matrices of the drug in biodegradable polymers such a polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissue.

The invention provides methods for oral administration of a pharmaceutical composition of the invention. Oral solid dosage forms are described generally in Remington's Pharmaceutical Sciences, 18th Ed., 1990 (Mack Publishing Co. Easton Pa. 18042) at Chapter 89. Solid dosage forms for oral administration include capsules, tablets, pills, powders, troches or lozenges, cachets, pellets, and granules. Also, liposomal or proteinoid encapsulation can be used to formulate the present compositions (as, for example, proteinoid microspheres reported in U.S. Pat. No. 4,925,673). Liposomal encapsulation may include liposomes that are derivatized with various polymers (e.g., U.S. Pat. No. 5,013,556).

In such solid dosage forms, the active compound is mixed with, or chemically modified to include, at least one inert, pharmaceutically acceptable excipient or carrier. The excipient or carrier may permit increased uptake of the compound, overall stability of the compound and/or circulation time of the compound in the body. Excipients and carriers include, for example, sodium citrate or dicalcium phosphate and/or (a) fillers or extenders such as starches, lactose, sucrose, glucose, cellulose, modified dextrans, mannitol, and silicic acid, as well as inorganic salts such as calcium triphosphate, magnesium carbonate and sodium chloride, and commercially available diluents such as FAST-FLO®, EMDEX®, STA-RX 1500®, EMCOMPRESS® and AVICEL®, (b) binders such as, for example, methylcellulose ethylcellulose, hydroxypropyhnethyl cellulose, carboxymethylcellulose, gums (e.g., alginates, acacia), gelatin, polyvinylpyrrolidone, and sucrose, (c) humectants, such as glycerol, (d) disintegrating agents, such as agar-agar, calcium carbonate, potato or tapioca starch, alginic acid, certain silicates, sodium carbonate, starch including the commercial disintegrant based on starch, EXPLOTAB®, sodium starch glycolate, AMBERLITE®, sodium carboxymethylcellulose, ultramylopectin, gelatin, orange peel, carboxymethyl cellulose, natural sponge, bentonite, insoluble cationic exchange resins, and powdered gums such as agar, karaya or tragacanth; (e) solution retarding agents such a paraffin, (f) absorption accelerators, such as quaternary ammonium compounds and fatty acids including oleic acid, linoleic acid, and linolenic acid (g) wetting agents, such as, for example, cetyl alcohol and glycerol monosterate, anionic detergent surfactants including sodium lauryl sulfate, dioctyl sodium sulfosuccinate, and dioctyl sodium sulfonate, cationic detergents, such as benzalkonium chloride or benzethonium chloride, nonionic detergents including lauromacrogol 400, polyoxyl 40 stearate, polyoxyethylene hydrogenated castor oil 10, 50 and 60, glycerol monostearate, polysorbate 40, 60, 65, and 80, sucrose fatty acid ester, methyl cellulose and carboxymethyl cellulose; (h) absorbents, such as kaolin and bentonite clay, (i) lubricants, such as talc, calcium sterate, magnesium stearate, solid polyethylene glycols, sodium lauryl sulfate, polytetrafluoroethylene (PTFE), liquid paraffin, vegetable oils, waxes, CARBOWAX® 4000, CARBOWAX® 6000, magnesium lauryl sulfate, and mixtures thereof; (j) glidants that improve the flow properties of the drug during formulation and aid rearrangement during compression that include starch, talc, pyrogenic silica, and hydrated silicoaluminate. In the case of capsules, tablets, and pills, the dosage form also can comprise buffering agents.

The solid dosage forms of tablets, dragees, capsules, pills, and granules can be prepared with coatings and shells, such as enteric coatings and other coatings well known in the pharmaceutical formulating art. Liquid dosage forms for oral administration include pharmaceutically acceptable emulsions, solutions, suspensions, syrups, and elixirs. In addition to the active compounds, the liquid dosage forms can contain inert diluents commonly used in the art, such as, for example, water or other solvents, solubilizing agents and emulsifiers, such as ethyl alcohol, isopropyl alcohol ethyl carbonate ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydroflirfuryl alcohol, polyethylene glycols, fatty acid esters of sorbitan, and mixtures thereof.

Also contemplated herein is pulmonary delivery of the compounds of the invention. The compound is delivered to the lungs of a mammal while inhaling. Contemplated for use in the practice of this invention are a wide range of mechanical devices designed for pulmonary delivery of therapeutic products, including, but not limited to, nebulizers, metered dose inhalers, and powder inhalers, all of which are familiar to those skilled in the art. All such devices require the use of formulations suitable for the dispensing of a compound of the invention. Typically, each formulation is specific to the type of device employed and can involve the use of an appropriate propellant material, in addition to diluents, adjuvants, and/or carriers useful in therapy.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods
Patient Characteristics

Patients (n=48) undergoing myeloablative allogeneic HSCT from 2005-2009 at Children's Hospital Boston (CHB) or Brigham and Women's Hospital (BWH) were recruited prospectively on an Institutional Review Board approved study. All participants and/or legal guardians gave consent and/or assent as appropriate. Age ranged from 1-60 years. Myeloablative regimens for hematologic malignancies (n=46) were chemoradiotherapy with TBI, 1400 cGy (n=38) or 1375 cGy (n=1) or combination chemotherapy including busulfan >14 mg/kg oral or IV equivalent (n=7). Myeloablation for aplastic anemia was cyclophosphamide 200 mg/kg (6 gm/M$^2$) plus ATG (n=2). Sixteen patients received BM and 32 received PB stem cells. Supportive care was per institutional routine. (48, 49). Prophylactic oral nonabsorbable antibiotics were administered: bacitracin and either polymyxin (BWH) or vancomycin (CHB). Blood counts and cultures were performed per routine in clinical laboratories. Sixteen patients had bacteremia with either Gram-positive (n=15) or Gram-negative (n=1) organisms. Temperature was recorded using the maximal value within ±1 day of sample acquisition. Endotoxin activity assay (EAA) measurements were added when the EAA became available.

Blood Collection and Plasma Preparation

PB samples were drawn into K2-EDTA or sodium heparin Vacutainers™, (Becton-Dickinson (BD), Franklin Lakes, N.J.) before conditioning (Baseline, B), on the day of HSCT (D0), and weekly ±1 day. PB was spun 1200 g for 5 min at 4° C., recovered, and stored in aliquots in pyrogen-free tubes at −80° C.

Human BPI ELISA

BPI was measured by ELISA (HyCult, Uden, The Netherlands), according to the manufacturers' instructions.

Endotoxin Measurement in Human PB

Endotoxin was measured by EAA according to the manufacturer's instructions (Spectral Diagnostics, Toronto, Canada). (27)

Human IL-6 ELISA

IL-6 was measured by flow cytometry (MoFlo, DakoCytomation, Glostrup, Denmark) using antibody coated fluorescent beads (Cytometric Bead Array BD Flex Sets, BD BioSciences, San Jose, Calif.) and Summit v4.0 software (DakoCytomation).

Measurement of mCD14 and TLR4

Monocyte surface expression of CD14 and TLR4 was measured with antigen-specific or isotype control monoclonal antibodies (eBioSciences, San Diego, Calif.) as previously described.(50)

In Vivo Radiation Mitigation Studies with rBPI$_{21}$ and Enrofloxacin

Male BALB/c mice (Stock #028, Charles River, Wilmington, Mass.) were acclimated prior to irradiation at age 12 weeks. Studies were conducted in accordance with Dana-Farber Cancer Institute's ACUC-approved policies and protocols. Mice were placed into a Rad Disk™ rodent microisolation irradiation cage (Braintree Scientific, Braintree, Mass.) and administered a single 7 Gy dose by a Gammacell® 40Exactor (Best Theratronics, Ottawa, Ontario) cesium source irradiator. Twenty-four hours thereafter, mice were either left untreated (7 Gy), or received one or more of the following treatments for 30 days: 1) rBPI$_{21}$, (XOMA (US) LLC, Berkeley, Calif.), 250 µl per injection of a 2 mg/ml stock constituted in formulation buffer and administered SC twice daily, 6-8 hours apart (rBPI$_{21}$/mouse was ~42 mg/kg/day); 2) 250 µl of the rBPI$_{21}$ formulation buffer (denoted VEH) consisting of 0.33 g/L citric acid, 1.01 g/L sodium citrate, 8.76 g/L sodium chloride, 2.0 g/L Poloxamer P188, and 2.0 g/L polysorbate 80, (all Sigma, St. Louis, Mo.) dissolved in water for injection, pH adjusted to 5.0, and filter sterilized; 3) Baytril® (enrofloxacin, MedVets, Sandy, Utah) at 10 mg/kg/day by oral gavage via 25 G feeding needles (Cadence Science, Cranston, R.I.) for the first 5-7 days, after which mice continued to receive antibiotic ad lib in water bottles until study termination or death. All mice were observed at least twice daily. Moribund mice were euthanized via CO$_2$ asphyxiation. At scheduled time points, mice were sacrificed humanely via isoflurane anesthetic overdose (IsoFlo®-Abbott Labs, Abbott Park, Ill.).

Blood and Tissue Preparation

CBCs were performed on a Hemavet 950 FS hematology analyzer (Drew Scientific, Waterbury, Conn.) with EDTA-anticoagulated (Becton-Dickinson, Franklin Lakes, N.J.) cardiac blood. Plasma was obtained by mixing blood with pyrogen-free heparin (APP Pharmaceutical, Schaumburg, Ill.), in pyrogen-free Eppendorf tubes (USA Scientific) and centrifugation at 14,000 rpm for 10 minutes. Single use aliquots were stored at −80° C. In some studies, femurs and tibiae from one leg/animal were dissected, fixed for 24 hours in 10% neutral buffered formalin (Fisher Scientific, Pittsburgh, Pa.), and processed, including coronal sectioning and hematoxylin and eosin (H&E) staining (Specialized Histopathology Services-Longwood, Boston, Mass.). Contralateral femurs and tibiae were taken for BM MNC enumeration and flow cytometry by flushing cells from the bones with cold RPMI 1640 medium supplemented with 10% FBS (JRH Biosciences, Lenexa, Kans.), L-glutamine, HEPES, pen/strep and gentamicin (all from Invitrogen, Carlsbad, Calif.). Red blood cells were lysed with hypotonic lysing buffer (Sigma). BM MNC were enumerated by trypan blue staining; viability was typically >90-95%.

Citrulline Determinations

Samples were analyzed with the MassTrak Amino Acid Analysis (AAA) system (Waters, Milford Mass. USA) with AccQTag™ derivatization and ultraviolet/visible detection.

Histopathologic Evaluations

A Board-certified hematopathologist (JK) assessed femoral BM cellularity on decalcified, formalin fixed, H&E stained paraffin-fixed sections using an Olympus BX51 microscope and an Olympus DP71 camera with DP Capture software. For each animal, 2 slides with 2 fields/slide were scored for the percent of BM space occupied by hematopoietic cells. A Board-certified pathologist (J-AV) enumerated apoptotic bodies/400× field in triplicate samples of H&E-stained paraffin-fixed colon sections. Samples from normal mice were identified, but all others were deidentified and presented in random order for analysis.

Endotoxin Measurement in Murine Plasma

Endotoxin was measured using the Limulus amoebocyte lysate (LAL) assay according to the manufacturer's instructions (Charles River, Boston, Mass.), and as previously described.(51)

BM FACS Analysis

Figure 10:
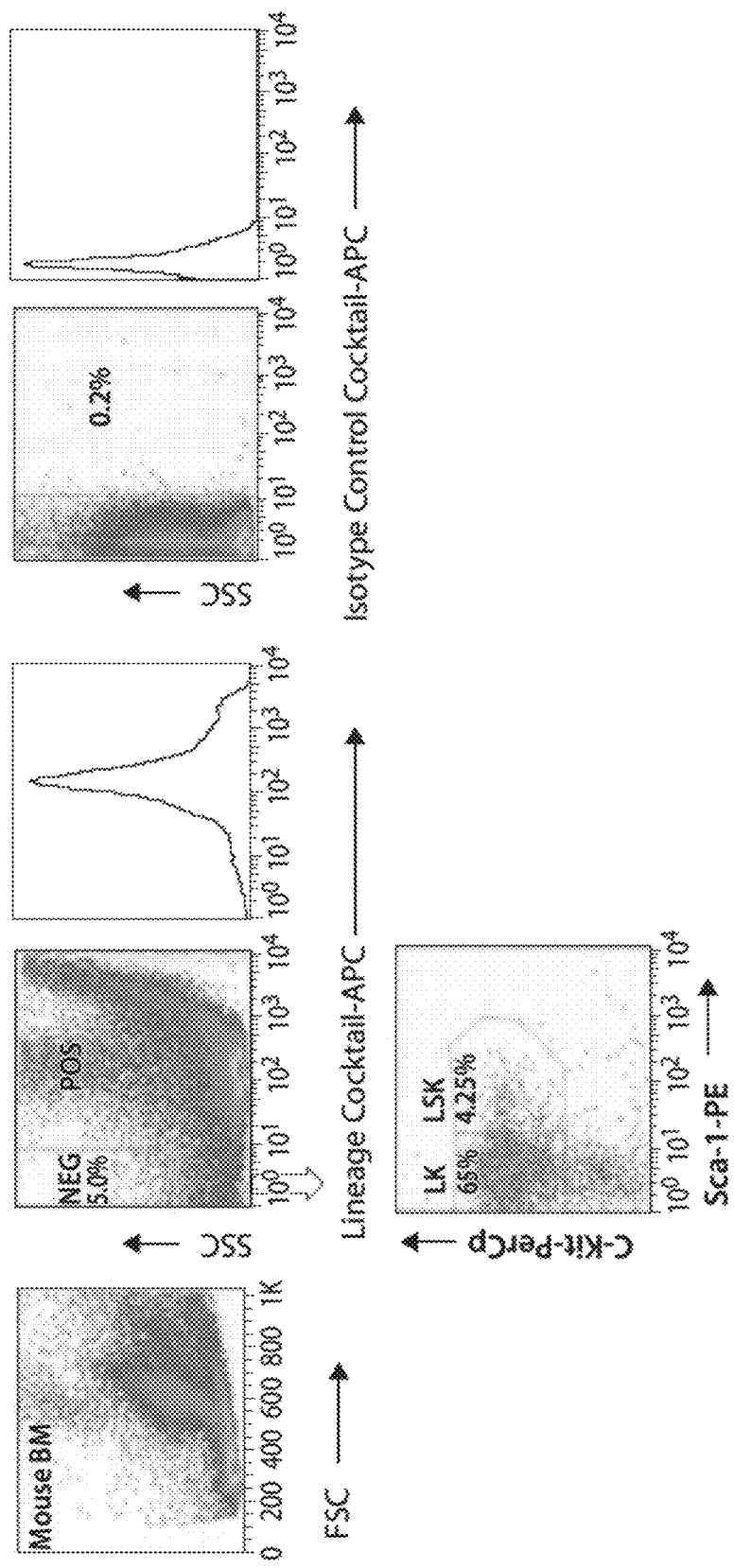
FIG. 10. Gating strategy for determining LK and LSK cells in BM from BALB/c mice by FACS. A gate is drawn on the FSC vs. SSC dot plot of BM cells in order to exclude small debris. Committed lineage cells were determined in the FL-4 channel (APC positive) vs. SSC, and gates drawn to bifurcate these from cells negative for lineage marker expression (neg-low APC fluorescence). Gating was confirmed through the use of a matched isotype control cocktail also conjugated to APC. Lineage negative cells are visualized on Sca-1PE×c-kit-PerCP5.5 dual fluorescence dot plots to assess the content of $Lin^-Sca-1^-c-kit^+$ (LK– progenitor cells) and Lin⁻Sca-1⁺c-kit⁺ (LSK– stem cells) in mouse BM. Histograms shown are from the analysis of a normal mouse.

BM cells were preincubated with 2% Rat anti-mouse CD16/CD32 and 1% normal rat serum for Fc blocking prior to staining cells bearing hematopoietic lineage markers (CD3ε, CD45/B220, CD11b, Ly-6G/Ly-6C, TER 119) with a cocktail of APC-conjugated lineage specific antibodies, or equivalent concentration of APC conjugated isotype control immunoglobins, 1:20 dilutions of PE-rat anti-mouse Sca 1 (clone D7) and PerCP-Cy5.5-rat anti-mouse c-Kit (clone 2B8), all from BD. Cells were stained for 25 minutes at 4° C., washed 2× with cold DPBS, and resuspended in 0.4% paraformaldehyde. 100,000 events were acquired on a FACScalibur™ flow cytometer (BD) and analyzed with FlowJo v.7.0.5 (Treestar) software. Cells negative for lineage marker expression were assessed for percentages of lin⁻Sca-1⁻c-kit⁺ (LK) and lin⁻Sca-1⁺c-kit⁺ (LSK) in BM (FIG. 10, gating strategy). Data from normal mice were consistent with published reports in naïve BALB/c mice.(52)

Statistics

For the human HSCT study, samples with undetectable analytes were assigned a value at half the lower limit of detection. For ANC, PLT, BPI, TLR4 and IL-6, data were analyzed after logarithmic transformation, as this yielded distributions that were more approximately normal. For these data, geometric means and error bars indicating +1 standard error of the mean (SEM) of the log values were then transformed back to original units and plotted on a logarithmic axis. The Wilcoxon signed rank test for matched pairs was employed when comparing values for the same patients at different time points, with values compared to baseline. Comparisons between subjects with or without fever were evaluated using the Mann-Whitney test. When assessing correlations between different parameters, within-subject correlations were calculated using the Spearman correlation coefficient and data from multiple time-points. The calculated coefficients were averaged over the different subjects and significance tested with the signed rank test. Unless otherwise noted, all p-values were two-sided. Statistical significance and graphic output were generated using Prism v. 4.0a (GraphPad Software; San Diego, Calif.) and SAS v. 9.1 (SAS Institute, Cary, N.C.). Statistical analysis for murine experiments was performed with Graph Pad Prism Version 5. Mantel-Cox log-rank was used to compare survival curves. Two tailed t tests (Mann-Whitney) are performed throughout except for citrulline data in which the data were analyzed by 1-sample t test as compared to theoretical mean of 100% and for hematologic analyses (Table 1) in which unpaired t tests were performed. Unpaired t tests do not assume equal variance. In all experiments, a P value of <0.05 was used to reject the null hypothesis. Where indicated in figures, *p<0.05, p<0.01, *p<0.001.

TABLE I

Peripheral blood counts after TBI by treatment group.

| | WBC (K/μL) | Neutrophils (K/μL) | Monocytes (K/μL) | Hb (g/dL) | PLT (K/μL) |
|---|---|---|---|---|---|
| 0 Gy | 4.08 (2.14-11.48) | 0.84 (0.46-2.4) | 0.24 (0.08-0.37) | 15.7 (14.6-17.8) | 914 (754-2015) |
| 7 Gy | | | | | |
| D15 | 0.36 ▲ (0.22-0.38) | 0.06 ▲ (0.03-0.08) | 0.025 ▲ (0.01-0.04) | 10.4 ▲ (8.8-11.3) | 195 ▲ (95-225) |
| D19 | 0.46 ▲ (0.32-0.61) | 0.115 (0.11-0.12) | 0.05 ▲ (0.04-0.06) | 7.7 ▲ (7.5-7.9) | 280.5 ▲ (224-337) |
| D30 | 3.98 (2.64-9.68) | 1.66 ▲ (1.16-4.86) | 0.66 ▲ (0.54-1.58) | 13.4 ▲ (13.1-14.3) | 692 (680-956) |
| ENR/BPI | | | | | |
| D15 | 0.3 ▲ (0.20-0.32) | 0.07 ▲▼ (0.06-0.08) | 0.01 ▲ (0-0.02) | 7.8 ▲● (6.7-9.4) | 229 ▲ (89-254) |
| D19 | 2.63 ■▼ (1.42-7.32) | 0.73 ■▼ (0.29-1.27) | 0.26 ■▼ (0.16-0.62) | 10.6 ▲■ (7.5-11.7) | 599.5 ▲■▼ (360-785) |
| D30 | 3.62 ▼ (0.72-5.5) | 1.69 ▲▼ (0.15-3.94) | 0.44 ▲ (0.07-1.75) | 13.7 ▲ (11.0-14.3) | 849 (407-1015) |
| ENR/VEH | | | | | |
| D15 | 0.22 ▲ (0.14-0.40) | 0.005 ▲ (0-0.09) | 0.005 ▲ (0-0.03) | 7.1 ▲●▼ (2.4-8.0) | 127 ▲ (61-231) |
| D19 | 0.38 ▲ (0.28-0.74) | 0.07 ▲▼ (0.02-0.18) | 0.02 ▲▼ (0.01-0.04) | 4.9 ▲●▼ (2.4-7.4) | 199 ▲ (95-261) |
| D30 | 2.3 (1.42-12.5) | 1.05 (0.4-6.31) | 0.4 (0.19-3.02) | 13.7 ▲ (12.8-14.1) | 753 (471-1175) |
| ENR | | | | | |
| D15 | 0.24 ▲ (0.14-0.30) | 0 ▲● | 0 ▲● | 8.80 ▲■ (5.6-10.9) | 196 ▲ (113-277) |
| D19 | 0.21 ▲ (0.18-0.32) | 0 ▲●■ | 0 ▲●▼ | 8.35 ▲■ (6.7-10.9) | 250.5 ▲ (185-318) |
| D30 | 1.84 ▲● (0.36-4.8) | 0.55 ● (0.06-2.34) | 0.14 ● (0.03-1.03) | 13.1 ▲ (2.9-15.5) | 713.5 ▲ (128-923) |

The following blood counts in Table I are values where the median falls into the normal range of the age-matched 0 Gy controls: for WBC: 7 Gy at D30, ENR/BPI at D19, ENR/BPI at D30, and ENR/VEH at D30; for Neutrophils: 7 Gy at D30, ENR/BPI at D19, ENR/BPI at D30, ENR/VEH at D30, and ENR at D30; for Monocytes: 7 Gy at D30, ENR/BPI at D19, ENR/BPI at D30, ENR/VEH at D30, and ENR at D30; for PLT: ENR/BPI at D30. ▲ statistically significant versus 0 Gy; ● statistically significant versus 7 Gy; ■ statistically significant versus VEH/ENR; ▼ statistically significant versus ENR. All p<0.05.

Results

Human Myeloablative HSCT is Associated with Early Neutropenia, Endotoxemia, Deficiency of BPI and Evidence of Host Responses to Endotoxin We examined endotoxin and BPI plasma levels in patients who underwent myeloablative conditioning for HSCT. Thirty-nine of 48 patients received chemoradiotherapy including 1375 (n=1) or 1400 (n=38) cGy TBI while 9 received ablative combination chemotherapy alone. As expected, myeloablative therapy followed by allogeneic HSC infusion resulted in a fall and recovery in PB counts (FIG. 1A). By the completion of myeloablative conditioning (D0), endotoxemia was readily detectable (FIG. 1B). Simultaneously, plasma BPI concentrations declined rapidly (D7 median decrease 71-fold, inter-quartile range 9-193-fold; FIG. 1B), correlating with the absolute neutrophil count (ANC; Spearman r=0.66; p<0.001). At the ANC nadir (D7), plasma BPI was undetectable (<100 pg/mL) in 37/48 patients (77%) and 80% of patients evaluated by endotoxin activity assay (27) were endotoxemic.

The TLR4 and mCD14 components of the TLR endotoxin receptor on peripheral blood (PB) monocytes exhibited increased and decreased surface expression, respectively, consistent with early PB mononuclear cell exposure to bioactive endotoxin (28, 29) (FIG. 1C). Subsequent elevation of IL-6 and fever, well-described downstream sequelae of TLR4 engagement by endotoxin, were maximal at the BPI nadir (D7, FIG. 1D). Intrapatient changes in IL-6 concentrations were positively correlated with the EAA (Spearman 0.48, p=0.01), and higher IL-6 levels concentrations were inversely correlated with BPI levels (Spearman −0.30, p<0.0001). Fever and BPI levels showed no association on D7, perhaps because nearly 80% of patients had undetectable BPI. However, on D14 patients with fever had lower BPI levels than afebrile patients (medians: undetectable vs. 3475 pg/mL, p=0.01). Notably, lower plasma BPI concentrations on D0, immediately prior to HSC infusion, were associated with longer time to neutrophil engraftment (p=0.03, Spearman r=−0.32), and with a trend towards longer time to platelet recovery (Spearman r=−0.26, p=0.08).

These findings suggest that BPI deficiency coupled with endotoxemia could contribute to endotoxin-related toxicity after myeloablation and raise the possibility that BPI supplementation might attenuate these toxicities. Whereas administration of HSC enables survival after myeloablation, HSC support would not be feasible after unintended radiation exposure. As radiation mitigation without HSC cannot be addressed experimentally in humans, we employed a murine model to examine the hypothesis.

Characterization of the Toxicity of 7 Gy Single Fraction TBI in BALB/c Mice

Figure 7:
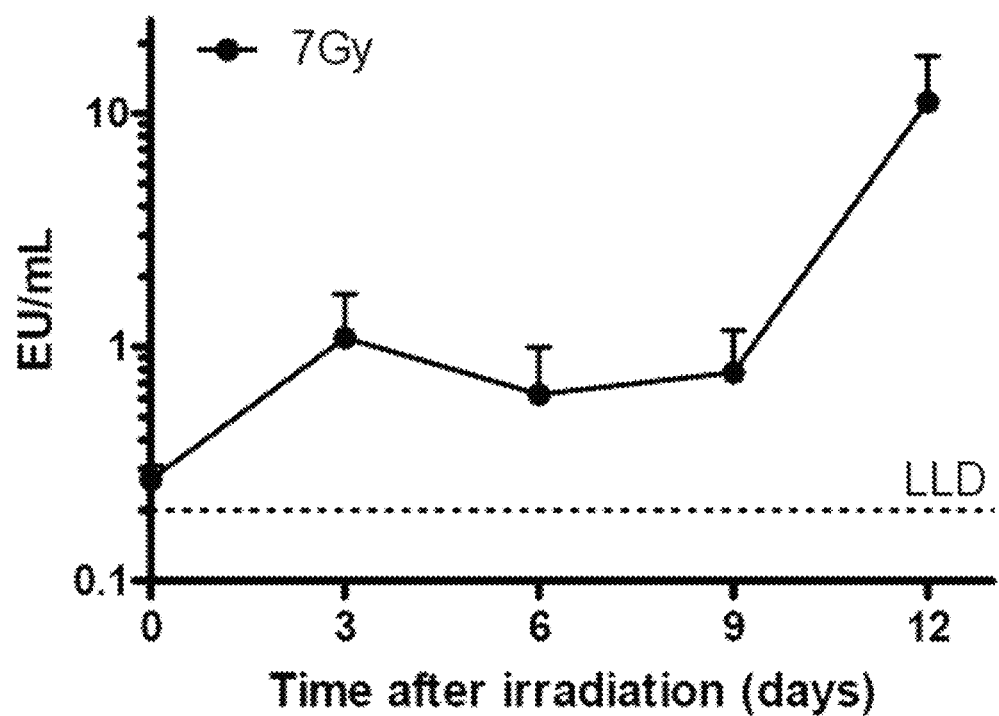
FIG. 7. 7 Gy irradiation of BALB/c mice is associated with subsequent endotoxemia. Blood samples were obtained for endotoxin assay by LAL on the days indicated and shown as mean±SEM. Endotoxin was present from D3 onwards. N=9 mice/timepoint on days 0, 3, 12, n=6 on D6, and n=8 on D9. Mortality of 7 Gy alone treatment precluded evaluation of sufficient mice for analysis beyond D12.

To model potentially lethal radiation exposure, we defined a dose of single fraction TBI associated with BM aplasia, GI toxicity, and a high rate of early mortality in BALB/c mice. A single fraction of 7 Gy was associated with 95-100% mortality by 30 days ($LD_{95/30}$) in 12 week old BALB/c (FIG. 2A). The lethality of 7 Gy exposure was reproducibly observed in each of the ensuing mitigation experiments: only 5/90 7 Gy irradiated mice (5.5%) survived to D30 and median survival in separate experiments ranged from 12-15 days. Following 7 Gy TBI, small bowel epithelial apoptosis assessed by histopathology was maximal at D3, and paralleled a fall in plasma citrulline levels, which are directly proportional to functional GI enterocyte mass (30). (FIG. 2B). Both GI mucosal findings improved by D6-9. Endotoxemia was also detectable by D3 and persisted until spiking higher just prior to death (FIG. 7). By D3, the BM was aplastic (FIG. 2C), with a concurrent fall of nearly 2 logs in BM mononuclear cell (MNC) content, including a decrement in hematopoietic stem (LSK, Lin$^-$ Sca-1$^+$ c-Kit$^+$) and progenitor (LK, Lin$^-$ Sca-1$^-$ c-Kit$^+$) cells (FIG. 2D, E, F).

The degree of mucosal injury, inflammation and toxicity experienced during human HSCT has been related to the intensity of myeloablation (31). To ensure the model was adequately myeloablative, we compared the effects of 7 and 6.5 Gy on hematopoiesis. Although histologic aplasia was identical at D3 regardless of TBI dose, mice had significantly greater BM MNC, LK and LSK 3, 10 and 15 days after 6.5 Gy than after 7 Gy (FIG. 2D, E, F). No significant recovery was observed in the 7 Gy cohort by D15. Subsequent mitigation experiments were performed after exposure to 7 Gy.

Figure 3:
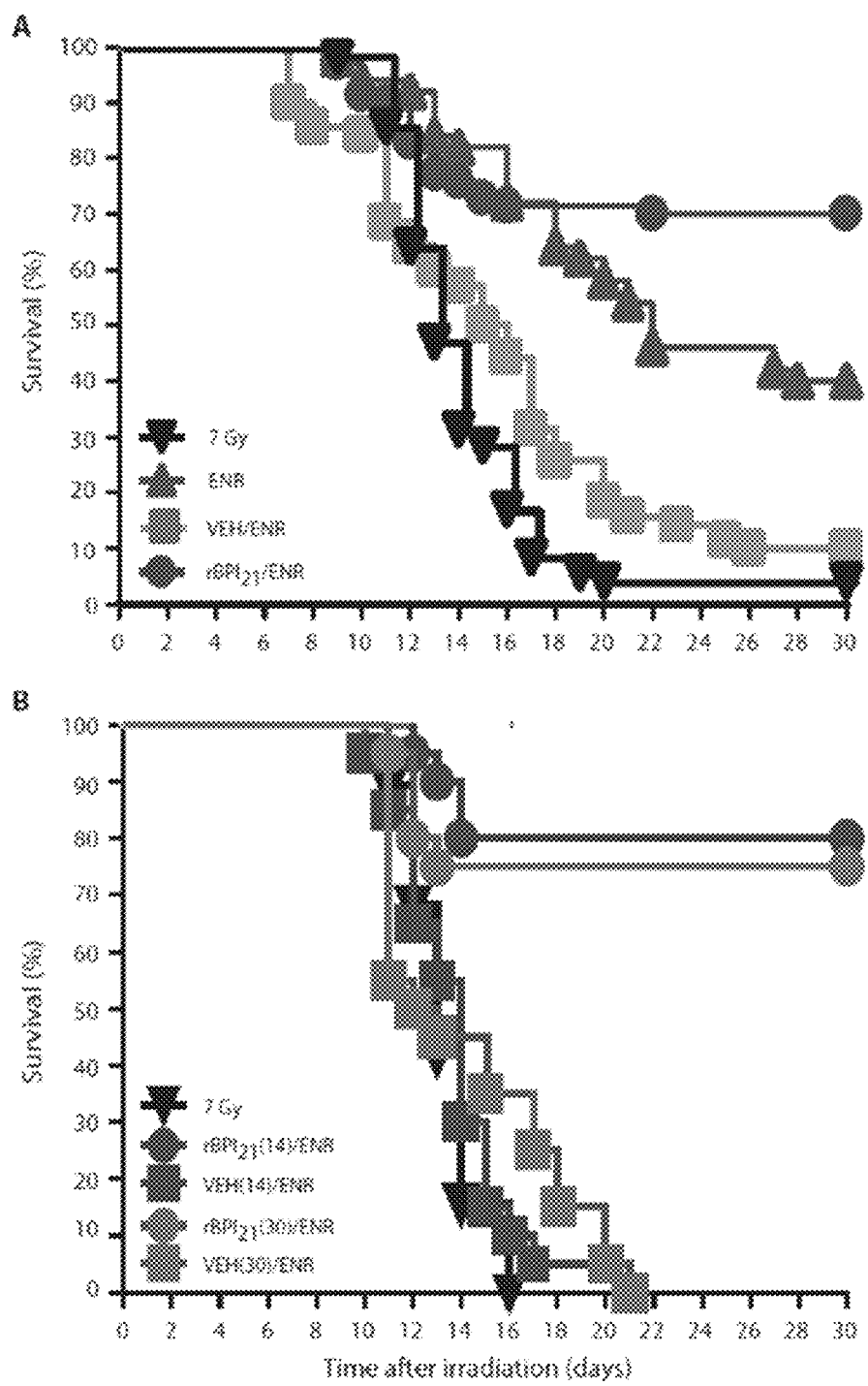
FIG. 3. $rBPI_{21}$ in combination with ENR enhances survival of BALB/c mice after 7 Gy TBI. (A) Survival of mice irradiated with 7 Gy given ENR plus $rBPI_{21}$ or VEH, ENR alone, or no treatment (denoted 7 Gy) 24 hours after irradiation and continuing for 30 days. In a composite analysis of three replicate experiments, survival of $rBPI_{21}$/ENR treated mice exceeded that of the other groups (P<0.0001 by Mantel-Cox log rank, n=70 mice per arm). Survival of the $rBPI_{21}$/ENR group also exceed that of VEH/ENR, ENR, and 7 Gy (P<0.0001, 0.008, and <0.0001, respectively by pairwise Mantel-Cox log-rank). (B) Survival of mice irradiated with 7 Gy given $rBPI_{21}$ or VEH (continued for either 14 or 30 days) plus ENR (continued for 30 days) or no treatment (denoted 7 Gy) 24 hours after irradiation. Survival was unaffected by duration of $rBPI_{21}$ treatment. Data was analyzed by pairwise Mantel Cox log-rank (n=20 mice per group).

$rBPI_{21}$ and Enrofloxacin (ENR) Administration Markedly Decrease TBI-Related Mortality The combination ($rBPI_{21}$/ENR) of $rBPI_{21}$ and oral ENR, a fluoroquinolone antibiotic analogous to ciprofloxacin, initiated 24 hours after an $LD_{95/30}$TBI dose of 7 Gy and continued through D30, produced a statistically significant improvement in D30 survival of mice (FIG. 3). In a composite analysis of 2 replicate experiments (aggregate n=50 mice/arm), survival of the $rBPI_{21}$/ENR group exceeded that of the VEH/ENR (VEH denotes the formulation buffer for $rBPI_{21}$), as well as the ENR or 7 Gy alone groups (<0.0001, 0.03 and <0.0001, respectively, by pair-wise Mantel-Cox log-rank). Only two deaths in 36 at-risk $rBPI_{21}$/ENR treated mice occurred after two weeks whereas losses in the other groups over this interval ranged from 38-79% of at risk animals. D30 survival after 7 Gy was not improved by either $rBPI_{21}$ (1/30 survivors) or its VEH (1/30 survivors) alone. Thus, $rBPI_{21}$ monotherapy was not pursued as a mitigation strategy at an $LD_{95/30}$ TBI dose.

Figure 8:
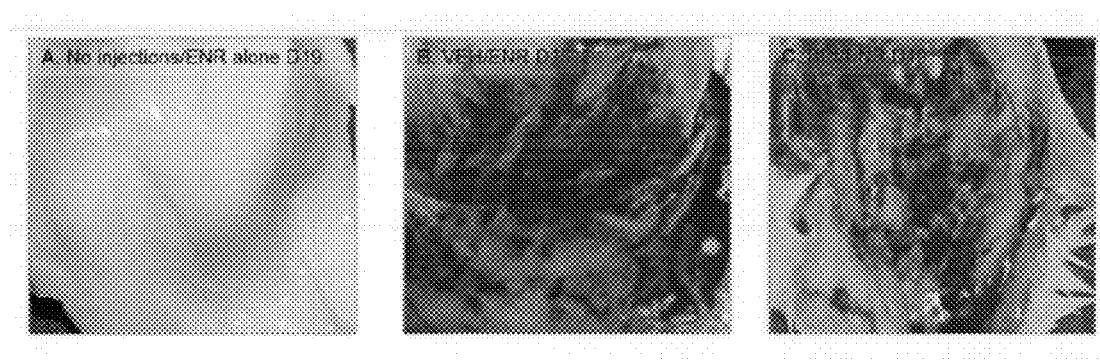
FIG. 8. Injection site injury and inflammation result from BID injection of $rBPI_{21}$ or VEH. During these radiation mitigation studies, some 7 Gy irradiated BALB/c mice received oral ENR only. Other 7 Gy irradiated mice received ENR as well as twice daily injections of 250 µl of $rBPI_{21}$ or its formulation buffer (denoted VEH) using sterile, single-use, insulin needles with fixed 28.5 G needles. Injections started 24 hours after radiation and continued until day 30. On either day 15 (B) or day 19 (A, C), mice were humanely sacrificed and the underside of the dorsal skin was exposed for photo documentation of localized tissue injury. Images taken with a Nikon D90 digital camera.

$rBPI_{21}$ has a 3 hour half-life in mice when administered by IV bolus or subcutaneous (SC) injection. As optimal continuous or q6hr IV or SC injection regimens were not feasible, we elected to use twice daily SC administration, initiating all treatments 24 hours after TBI and continuing through D30. As illustrated in FIG. 3, the control for the $rBPI_{21}$/ENR regimen, VEH/ENR, was associated with worse 30 day survival than oral ENR alone (p=0.0002, by pair-wise Mantel-Cox log-rank for 2 replicate experiments with combined n=50/arm), suggesting that repetitive handling and local skin trauma entailed in SC administration were associated with significant toxicity. Local skin injury was readily observed in irradiated mice repetitively injected with $rBPI_{21}$ or VEH in comparison to irradiated mice treated with ENR alone (FIG. 8).

A curtailed schedule, stopping injection after 14 days (denoted $rBPI_{21}$(14) and VEH(14) in FIG. 3B) was explored. Reasoning that oral antibiotic treatment could be more readily deployed in a mass-casualty setting, the ENR schedule was not changed. $rBPI_{21}$ (14)/ENR provided the same survival advantage as the longer schedule (FIG. 3B). Six irradiated mice that had received $rBPI_{21}$(14)/ENR were followed beyond D30, and five of the six mice remained alive and healthy-appearing at D131.

$rBPI_{21}$/ENR Administration Mitigates Hematopoietic Toxicity after TBI

To characterize effects on hematopoiesis, we enumerated BM MNC retrieved from flushed BM cavities (FIG. 4). At D10, all irradiated groups, regardless of treatment, exhibited fewer BM MNC than unirradiated, age-matched controls (p<0.0001). However BM MNC content was significantly greater in the $rBPI_{21}$/ENR treated mice than in mice receiving either 7 Gy alone or with ENR or VEH/ENR (p=0.0003, 0.001 and <0.0001, respectively). This same pattern was repeated on D15 and D19, as the $rBPI_{21}$/ENR treated mice consistently had statistically significantly greater BM MNC content than the other groups (FIG. 4). Only $rBPI_{21}$/ENR treatment was associated with consistently greater BM MNC content than observed after 7 Gy alone.

Figure 5:
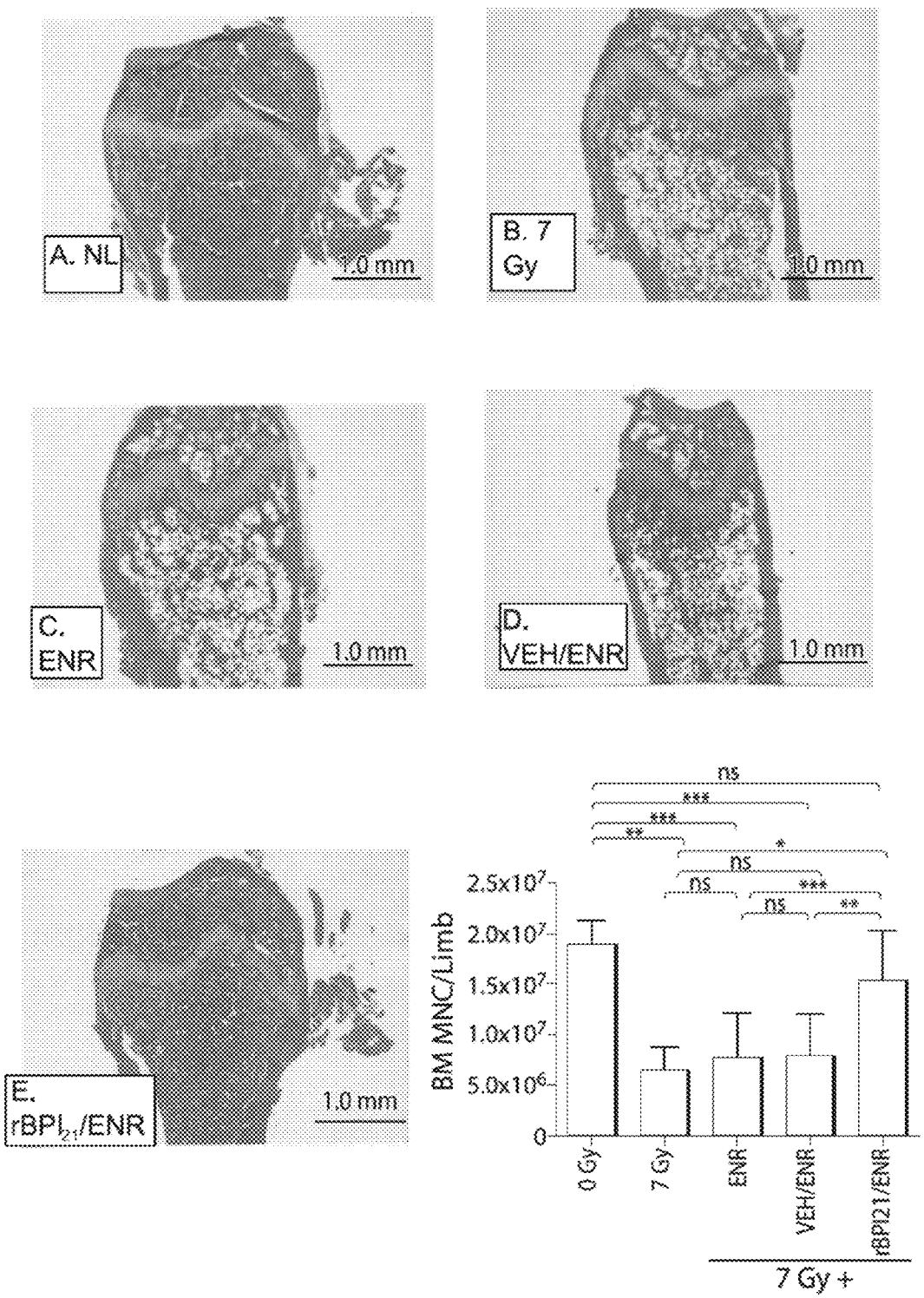
FIG. 5. $rBPI_{21}$/ENR treatment results in restoration of BM cellularity to normal levels by D30 after irradiation. BM histopathology (one hind limb) and MNC count (contralateral hind limb) were assessed in mice surviving to D30. Representative femur histology is shown for (A) untreated, age-matched controls (normals) or (B) 7 Gy irradiated mice. Other mice received both 7 Gy TBI and the following treatments started 24 hrs after irradiation: (C) ENR, (D) VEH/ENR or (E) $rBPI_{21}$/ENR. In addition to histology, corresponding counts of BM MNC flushed from a hind leg of individual mice were determined (F). Bars show mean±SD for n=4, 3, 12, 16, and 7 mice/group, respectively. The early, high mortality of 7 Gy alone and VEH/ENR treated mice limited the size of these cohorts. Only $rBPI_{21}$/ENR treatment resulted in BM MNC counts that were statistically indistinguishable from 0 Gy. $rBPI_{21}$/ENR MNC counts also differed from counts in 7 Gy, ENR, and VEH/ENR (p=0.01, p=0.0002, p=0.001, respectively). Data from two replicate studies are shown. Similar results were obtained in all studies. Data analyzed by Mann-Whitney.
Figure 9:
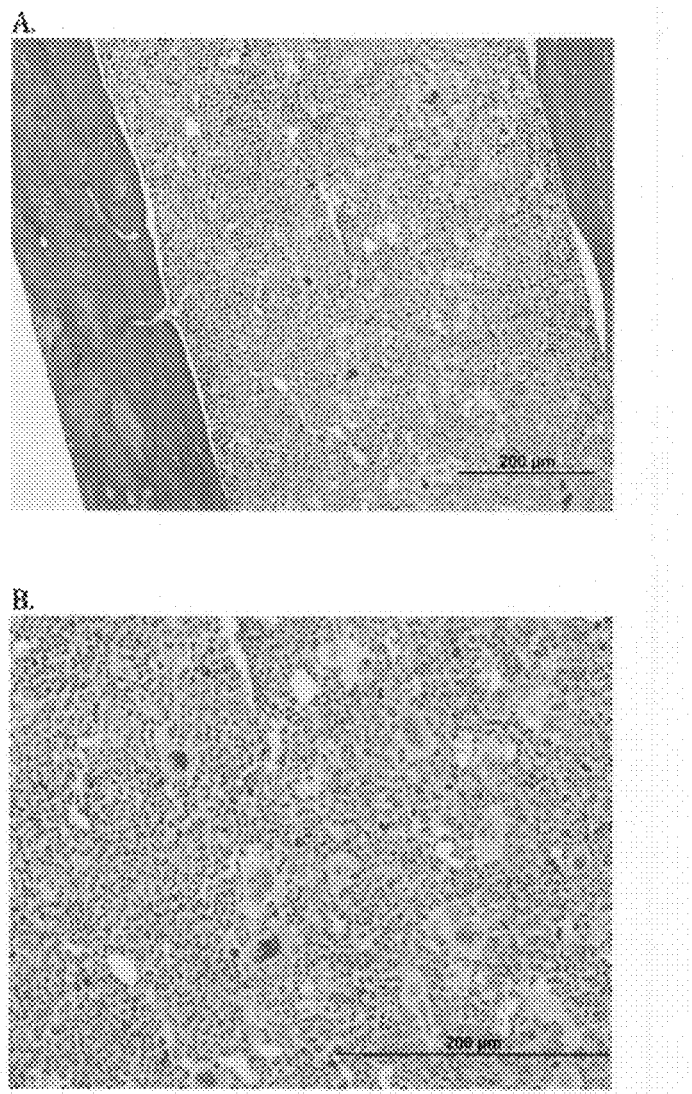
FIG. 9. Trilineage hematopoiesis in cellular BM of $rBPI_{21}$/ENR treated mice. BALB/c mice were irradiated to 7 GY and initiated $rBPI_{21}$/ENR 24 hours thereafter. Mice were euthanized 19 days after irradiation. Low power images of H&E stained coronal sections of femur in $rBPI_{21}$/ENR treated mouse were shown in FIG. 3. These images show higher power images at (A) 20× and (B) at 40×. BM demonstrates trilineage hematopoiesis without dysplasia, relative myeloid hyperplasia and robust recovery of megakaryocytes.

This rapid increase in BM MNC was reflected in the cellularity of BM assessed by histopathology on D19 (FIG. 4). $rBPI_{21}$/ENR treated irradiated mice demonstrated well-recovered BM cellularity, ranging from 80-90%, whereas that of the 7 Gy alone, ENR, and VEH/ENR treated mice was estimated at 20, <5, and 10-50%, respectively. Trilineage hematopoiesis was observed in all mice with sufficient cellularity, and a subset of mice, most notably those receiving $rBPI_{21}$/ENR, had myeloid predominance and increased megakaryopoiesis (FIG. 9). By D30, all surviving mice demonstrated improved cellularity, as previously described in murine TBI survivors (32). However, $rBPI_{21}$/ENR treated mice demonstrated more robust cellularity with significantly greater BM MNC than ENR or VEH/ENR (FIG. 5). Recovering cellularity was also seen in the more limited pool of 7 Gy survivors at D30.

Figure 6:
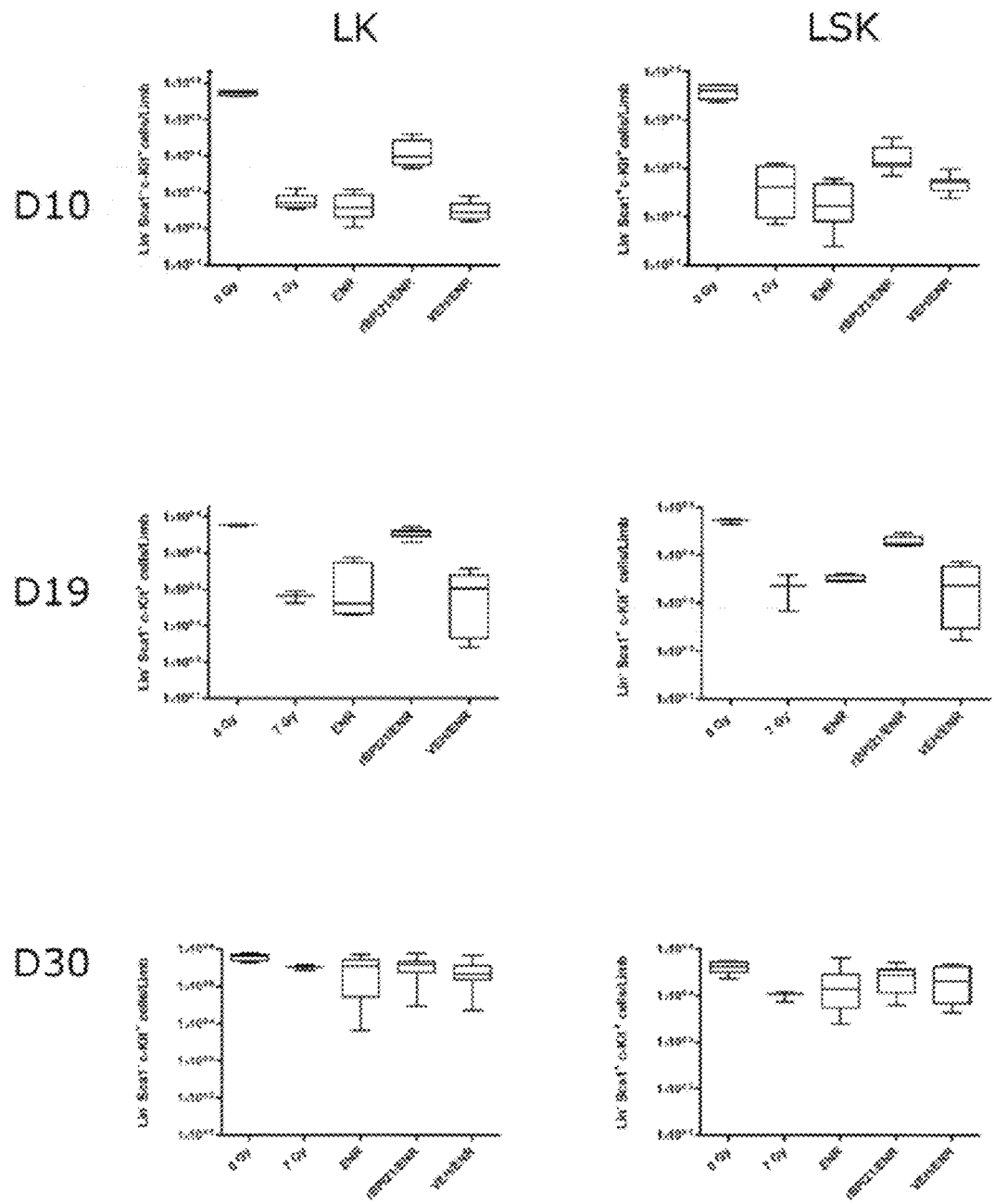
FIG. 6. $rBPI_{21}$/ENR treatment is associated with more rapid expansion of early hematopoietic cells after 7 Gy TBI. Flow cytometry was used to quantify LK (left panels) and LSK (right panels) cells contained within BM MNC of age-matched untreated controls (0 Gy) or mice administered 7 Gy and initiated on no treatment (7 Gy), ENR, $rBPI_{21}$/ENR or VEH/ENR treatments 24 hours thereafter. Results from D10, top panels, D19, middle panels, and D30, bottom panels, are shown. Box and whisker graphs depict the range, $25^{th}$ and $75^{th}$ percentiles and median number of LK or LSK phenotype cells within BM from one hind limb of each animal in each treatment group. N=4 for 0 Gy controls at all timepoints. N=8 mice/treatment on D10. N=6-8 mice/treatment at D19. Greater inequality in survival to D30 resulted in n=3 (7 Gy), 12 (ENR), 16 ($rBPI_{21}$/ENR), and 7 (VEH/ENR) mice/group. Compared to 7 Gy, ENR or VEH/ENR, $rBPI_{21}$/ENR treatment was associated with greater numbers of both LK and LSK cells at the earlier time points (p=0.004 for all comparisons on D10 and p=0.004, 0.0003 and 0.0001 on D19, respectively). D30 LK and LSK content of all groups, including controls, was equivalent. Data from two replicate experiments are shown. Similar results were obtained in all studies. Data analyzed by Mann-Whitney.

While the number of LSK and LK remained below the age-matched unirradiated controls at each time point, administration of $rBPI_{21}$/ENR was associated with increased numbers of LSK and LK BM cells in the first weeks after TBI (FIG. 6). The absolute number of both LSK and LK per hind limb in rBPI$_{21}$/ENR mice was significantly greater than that in 7 Gy alone, ENR or VEH/ENR treated mice at D10 and D19. No other treatment was associated with a difference from the untreated irradiated group. At D30, there was no difference among surviving mice between treatment groups or between treatment and normal controls.

Figure 12:
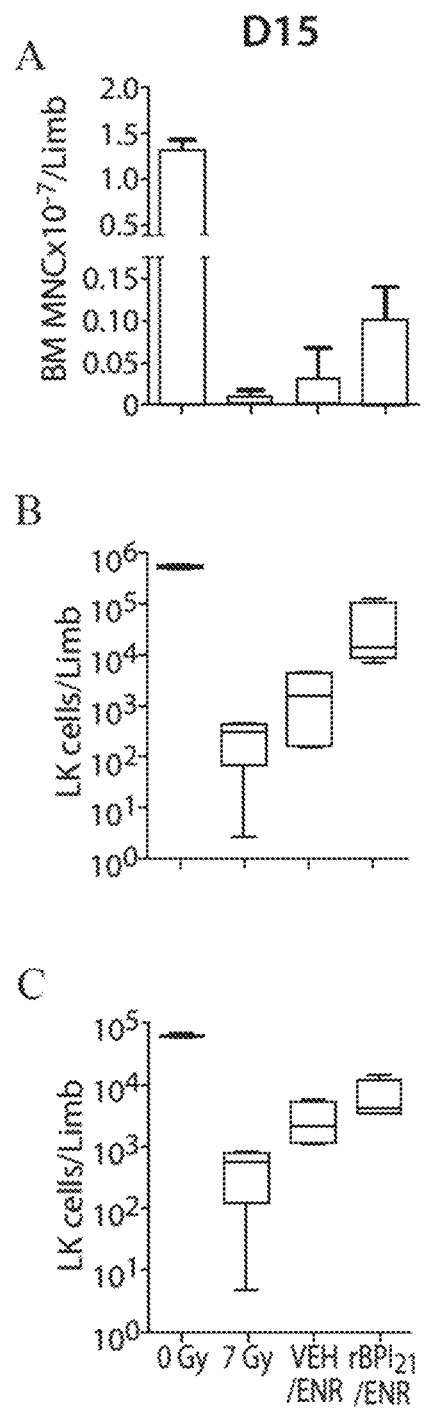
FIG. 12. Effects of 14 and 30 days of $rBPI_{21}$ plus ENR on bone marrow mononuclear cells, L K and LK cells are equivalent. BALB/c mice were irradiated to 7 Gy and treatments were initiated 24 hours thereafter. Some mice received twice daily subcutaneous $rBPI_{21}$ in combination with ENR until D15 at which time the remainder were divided equally into one group called $rBPI_{21}$ (14)/ENR in which $rBPI_{21}$ was discontinued but ENR was continued until D30, and another group, rBPI21 (30)/ENR, in which both $rBPI_{21}$ and ENR were continued until D30. The VEH/ENR group was treated as previously described. $rBPI_{21}$ (14)/ENR and $rBPI_{21}$ (30)/ENR had comparable levels of bone marrow mononuclear cells (panels A, D), LK (panels B, E) and LSK (panels C, F) at all timepoints. Quantification was performed as per Methods. Bar graphs+SD depict bone marrow mononuclear cells, and box and whisker graphs depict the range, 25th and 75th percentiles and median number of LK or LSK phenotype cells within bone marrow from one hind limb of each animal in each treatment group. For the $rBPI_{21}$ (14)/ENR and $rBPI_{21}$ (30)/ENR groups, D15: n=4/group, D18: n=5-6/group, and D30: 8-10/group. Due to early mortality, there was n=1 (7 Gy) and n=2 (VEH/ENR) at D18 and no survivors in those groups at D30. Values obtained from 2 normal animals are depicted as the 0 Gy values. Data obtained from a single study are shown.
Figure 12:
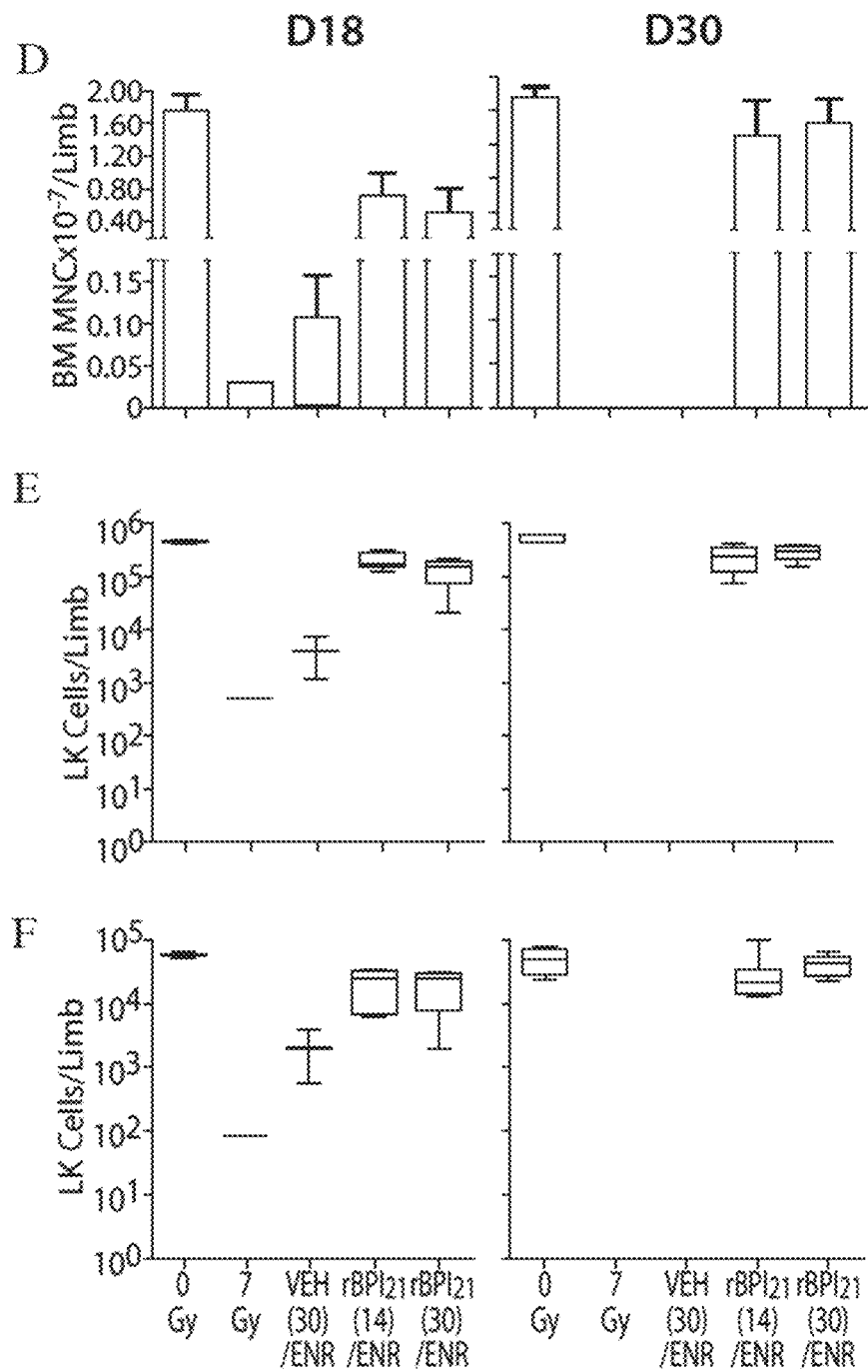
Figure 13:
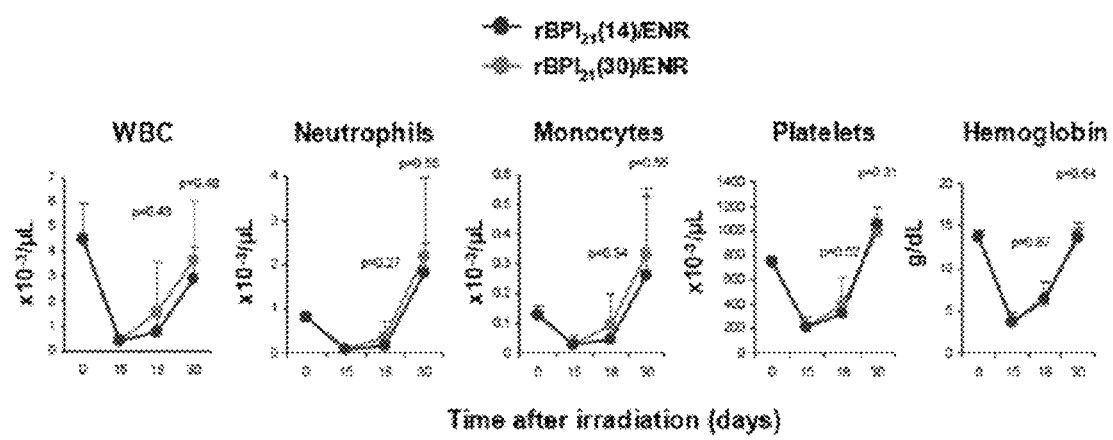
FIG. 13. Peripheral blood counts are equivalent after 14 or 30 days of $rBPI_{21}$ plus ENR treatment. Comparable levels of white blood cells (WBC), neutrophils, monocytes, platelets, and hemoglobin were measured in the peripheral blood of BALB/c mice treated with $rBPI_{21}$ for 14 days, $rBPI_{21}$ (14)/ENR-red circles, as compared to treatment with $rBPI_{21}$ for 30 days, $rBPI_{21}$ (30)/ENR-gray circles. Treatments began 24 hours after 7 Gy irradiation. Peripheral blood counts were obtained as described in Methods. All mice received twice daily subcutaneous $rBPI_{21}$ in combination with ENR until D15 at which time 4 mice were bled for peripheral blood cell analysis. The remainder were divided equally into one group called $rBPI_{21}$ (14)/ENR in which $rBPI_{21}$ was discontinued but ENR was continued until D30, and another group, $rBPI_{21}$ (30)/ENR, in which both $rBPI_{21}$ and ENR were continued until D30. Results show the mean+standard deviation of the peripheral blood count values measured on D18: n=5-6/group, and D30: 8-10/group. Values obtained from 2 normal animals are depicted as the D0 values. Data obtained from a single study are shown.
Figure 14:
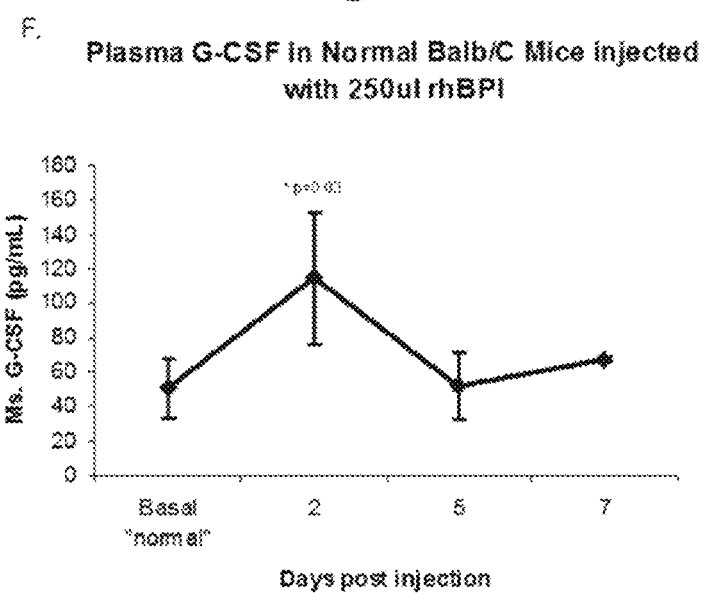
FIG. 14. (A-F) Granulocyte stimulating factor (G-CSF) levels are increased in response to $rBPI_{21}$ treatment in irradiated and in unirradiated mice.
Figure 15:
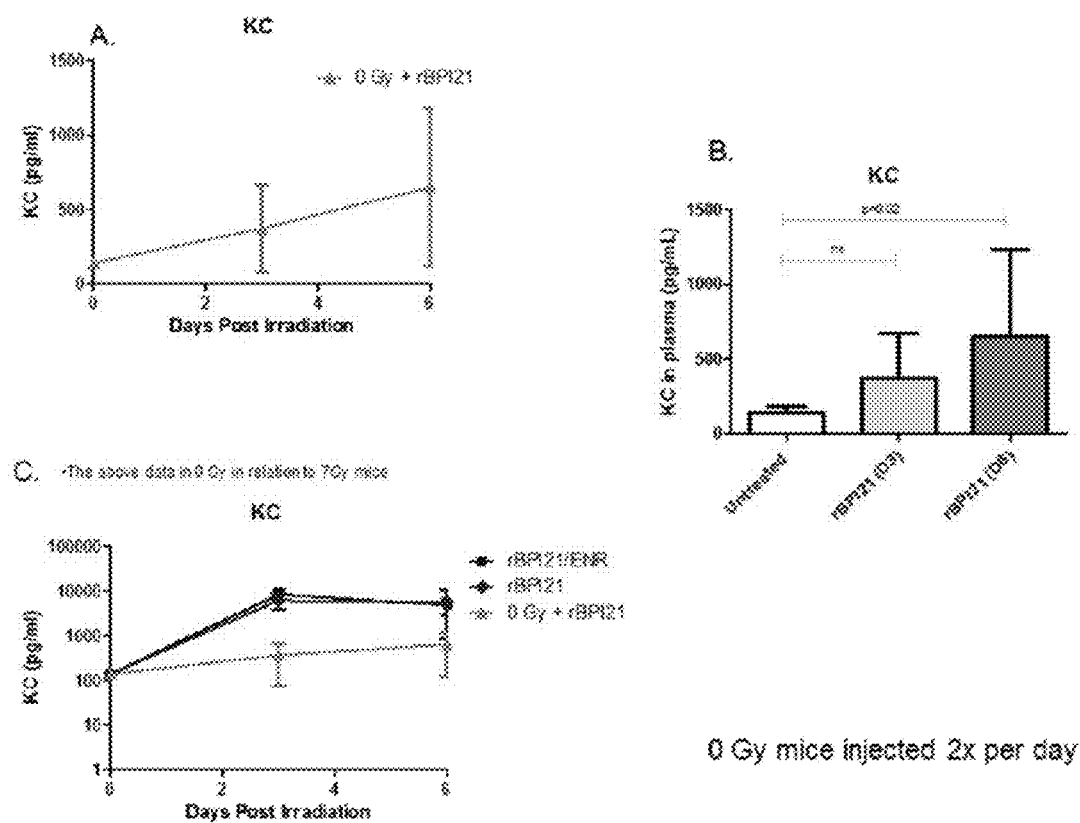
FIG. 15. (A-C) Murine keratinocyte chemoattractant (murine KC) levels are increased in response to $rBPI_{21}$ treatment in in unirradiated mice. The stimulation of murine KC by $rBPI_{21}$ treatment is augmented by prior irradiation.
Figure 16:
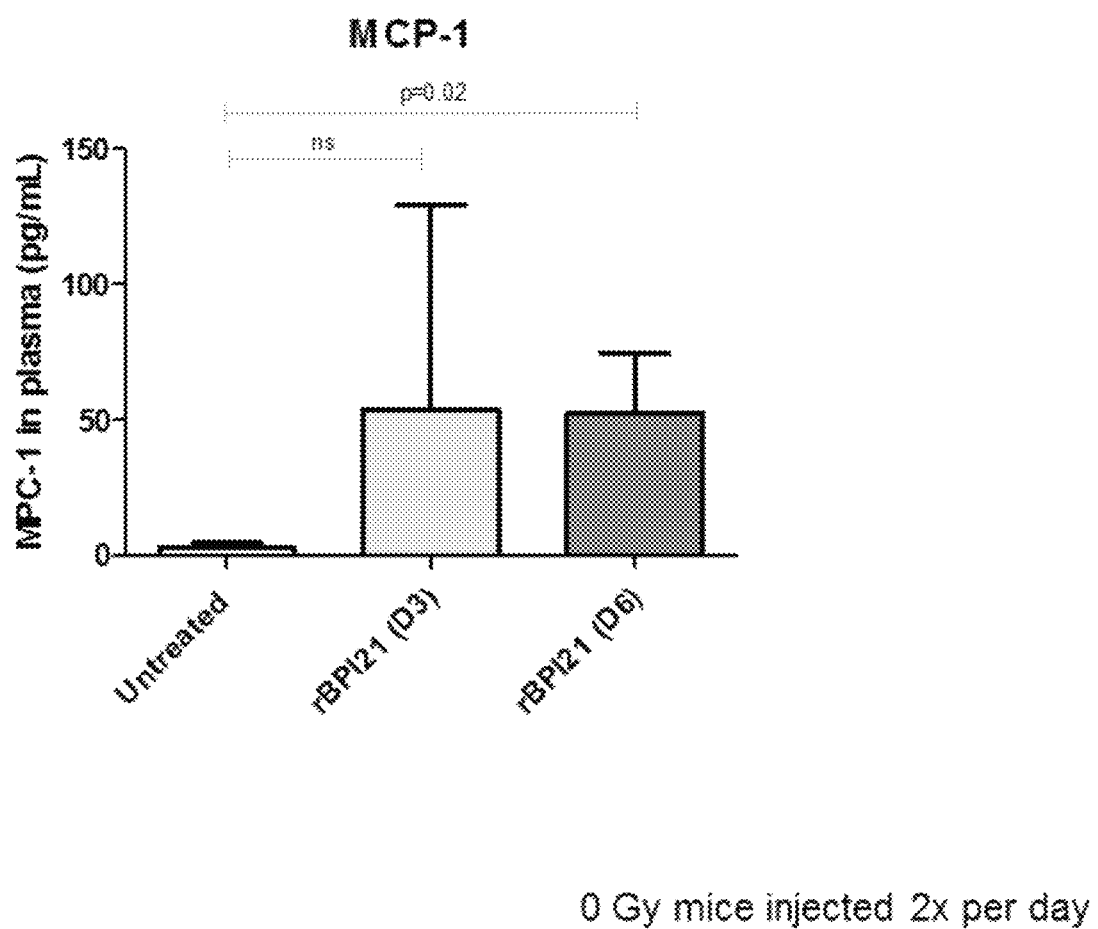
FIG. 16. Monocyte chemotactic protein-1 (MCP-1), also known as Chemokine (C-C motif) ligand 2 (CCL2) levels are increased by $rBPI_{21}$ treatment.

BM changes correlated with changes in peripheral blood counts. The effects of 7 Gy on PB counts could be seen in virtually every hematologic parameter measured (Table 1). rBPI$_{21}$/ENR treatment was associated with greater recovery of white blood cell (WBC), neutrophil, monocyte and platelet counts by D19 than was 7 Gy alone, ENR or VEH/ENR treatment. In contrast to the other groups, median WBC, neutrophil and monocyte levels of rBPI$_{21}$/ENR treated mice were in the normal range. Median hemoglobin was also greater in the rBPI$_{21}$/ENR treated mice, although this difference did not reach statistical significance. The WBC and neutrophils of rBPI$_{21}$/ENR treated mice remained significantly greater than the ENR treated animals at D30, at which point there were too few 7 Gy alone or VEH/ENR mice for meaningful comparison to other groups. Equivalent mitigation of hematopoietic toxicity was observed with the shorter rBPI$_{21}$(14)/ENR schedule (FIGS. 12 and 13).

rBPI$_{21}$ Administration Markedly Increases Inflammatory-Associated Chemokines rBPI$_{21}$ treatment significantly increases inflammatory-associated chemokines such as granulocyte colony stimulating factor (G-CSF) (FIG. 14), murine keratinocyte chemoattractant (murine KC; human homologs include Gro-alpha, IL-8) (FIG. 15), and monocyte chemotactic protein-1 (MCP-1, also known as Chemokine (C-C motif) ligand 2 or CCL2) (FIG. 16). BPI stimulation of G-CSF and murine KC in plasma is augmented by but not isolated to prior radiation. Without intending to bound by theory, this may represent one mechanism by which hematopoietic effects are realized. The plasma levels achieved after irradiation and rBPI administration are consistent with infusion of pharmacologic amounts of recombinant G-CSF IV. The data demonstrates highly significant increases (1-3 log increments) in G-CSF in irradiated mice given SC BID rBPI alone or in combination with enrofloxacin. Therefore the elevation of GCSF is a function of the rBPI and not dependent upon the combination of BPI with ENR. A less marked but statistically significant elevation of G-CSF was also seen in unirradiated mice given either a single injection of rBPI or BID SC injections.

An observational cohort study in patients undergoing HSCT was conducted to identify molecular and cellular changes that might be relevant to the toxicity of myeloablative irradiation. We observed that the neutropenia routinely following myeloablative treatment was associated with rapid depletion of plasma BPI, a neutrophil-derived protein with potent endotoxin neutralizing activity, (25, 26) at a time concurrent with endotoxemia. These changes paralleled cellular (mCD14, TLR4 surface levels), plasma (IL-6) and physiologic (fever) alterations consistent with increased systemic endotoxin activity (24, 25). We also observed that lower plasma BPI concentrations at the time of HSC infusion (D0) correlated with more delayed myeloid engraftment, suggesting that endotoxin might directly or indirectly exert some negative influence on HSC at time of infusion and for a period thereafter. The ability of exogenous BPI supplementation to mitigate radiation toxicity in humans exposed to TBI doses that produce mucosal injury, endotoxemia and prolonged BM aplasia was then explored. Using an LD$_{95/30}$ single fraction myeloablative TBI model in BALB/c mice, we demonstrated that a combination of rBPI$_{21}$ and ENR, initiated 24 hours after radiation exposure was associated with survival of two-thirds or more of the animals (p<0.0001). We selected rBPI$_{21}$ and a fluoroquinolone antibiotic as an immediately actionable strategy; both agents have biologic activity and highly favorable safety profiles in healthy and ill humans, including those with multi-organ compromise (33-43). rBPI$_{21}$ alone did not improve survival, whereas ENR alone provided some survival benefit. Mitigation effects of fluoroquinolones alone have been variable, potentially related to differences including the animal model and treatment design (15, 16). In this study, the survival benefit of ENR treatment was significantly less than that of rBPI$_{21}$/ENR, despite the repetitive injury of the injection regimen. Moreover, irradiated animals treated with VEH/ENR or ENR were characterized by delayed recovery of every hematopoietic parameter examined. Only rBPI$_{21}$/ENR was consistently associated with both improved survival and more rapid and complete hematopoietic recovery. These may be related findings as suggested by survival of 97% of rBPI$_{21}$/ENR treated animals after the reconstitution of near normal BM cellularity and PB counts documented on D19.

The contributions of hematopoietic syndrome to the morbidity and mortality of ARS in humans (1, 2, 4, 44-46) underscores the relevance of the observed effects of rBPI$_{21}$/ENR on hematopoiesis. Allogeneic HSCT mitigates BM failure resulting from myeloablation, (5) but it is unlikely that resource-intensive HSCT could be implemented rapidly or successfully during a mass radiation exposure (44-46). Multiple agents (47), including fluoroquinolones (16) and the TLR agonists flagellin (19, 21) and endotoxin (17), provide some radioprotection in animal models if administered prior to TBI. In contrast, few agents have demonstrated efficacy when administered after radiation (i.e. radiation mitigation) and efficacy has generally been dependent upon administration within minutes to hours after radiation exposure. Unfortunately, such rapid deployment of a mitigation strategy is unlikely, making strategies that can be delayed for 24 hours or more highly desirable.

Figure 11:
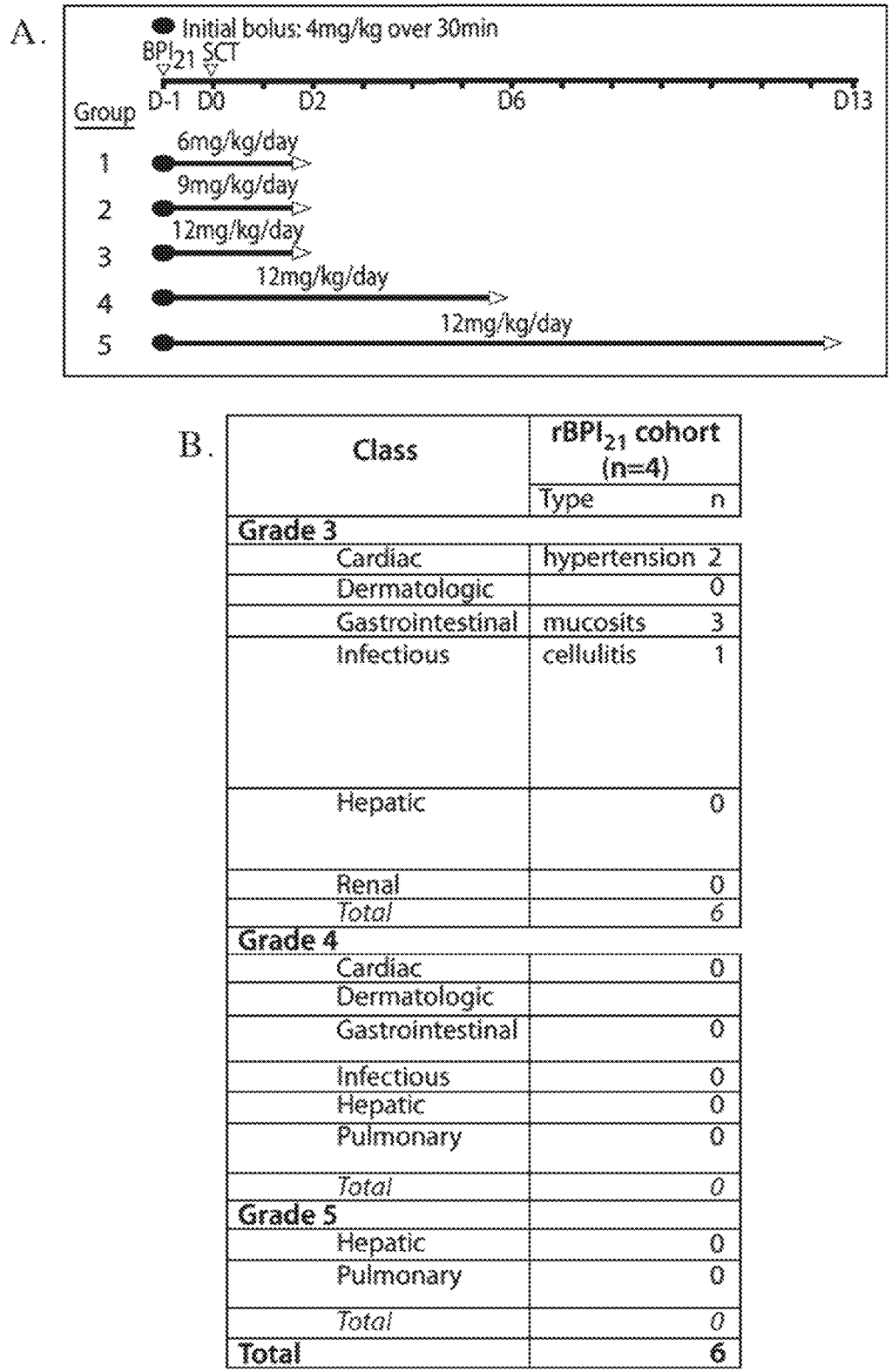
FIG. 11. Limited pilot clinical trial of $rBPI_{21}$ infusion in patients undergoing allogeneic HSCT supports tolerability after myeloablative therapy. Four of the six patients enrolled into the first cohort of an IRB-approved, multi-institutional Phase I-II pilot trial of $rBPI_{21}$ administration in the setting of myeloablative HSCT received radiation based treatment. All had hematologic malignancies, were aged 50-65 yrs (median 55), and signed consent. Subjects received cyclophosphamide and 1360 (n=3) or 1400 (n=1) fractionated TBI for myeloablative conditioning. (A) All patients received 4 mg/kg bolus IV $rBPI_{21}$ Day −1 followed by continuous IV infusion of 6 mg/kg/day for 72 hours. Dose and duration of continuous infusion were to be escalated according to the design shown but the trial was discontinued by the Sponsor (XOMA (US) LLC) when the study lot of drug outdated. (B) Significant adverse events experienced during the HSCT admission are shown.

There is no established radiation dosimetry technology that can accurately triage exposed individuals and determine those most likely to benefit from mitigation treatment, nor is there a human therapeutic application of TBI without HSC support in which to study the efficacy and toxicity of radiation mitigation agents. These limitations highlight the importance of selecting strategies unlikely to produce toxicity in either minimally affected or critically-ill populations. The components of the strategy studied here meet this criterion. The human equivalent of ENR, a veterinary fluoroquinolone, is ciprofloxacin which was FDA approved in 1987. Fluoroquinolones have excellent oral bioavailability, are well-tolerated and have been widely and safely used after myeloablative chemoradiotherapy (42, 43). rBPI$_{21}$ is available in a soluble form with demonstrated stability when stored at 2-8° C. facilitating stockpiling. It may be administered SC, IV and IP and in animals has shown efficacy in an intranasal form. In addition to efficacy in animal models of pure endotoxemia and Gram-negative bacteremia, rBPI$_{21}$ can abrogate the signs and symptoms of endotoxemia in humans and decrease or eliminate associated cytokine dysregulation and coagulopathy (38, 39). No significant toxicity has been seen in Phase I-III trials enrolling >1100 normal volunteers and critically ill patients, including infants and subjects with meningococcemia or undergoing major operative procedures (33-41). In a pilot experience (n=4), we have also administered rBPI$_{21}$ to patients receiving TBI as part of myeoloablative HSCT without any attributable toxicity (FIG. 11). In aggregate, these data suggest $rBPI_{21}$/ENR could be safely administered to individuals with poorly documented degrees of radiation exposure.

Increased global concerns about radiation injury consequent to natural disasters, nuclear conflict or terrorism or as an untoward consequence of intentional medical exposure led us to investigate whether supplemental BPI could be translated to an effective radiation mitigation strategy. Our data suggest that the combination of $rBPI_{21}$ and a fluoroquinolone antibiotic, started as late as 24 hours after a possibly lethal radiation exposure, has the potential to both improve survival and limit the scope and duration of requisite supportive care. Given the relatively low sensitivity of mice to endotoxin in comparison to humans, the sub-optimal dosing, and the repetitive stress and inflammatory response of SC injection in this model, our results may underestimate the potential benefit of this combination. The observed efficacy of treatment initiated 24 hours post-TBI is shared by few other approaches and weighs heavily in its favor. The human safety record of $rBPI_{21}$ and fluoroquinolones provides a platform for rapid adoption that is particularly compelling given the obligate overtreatment resulting from current limitations of radiation dosimetry and affords decreased likelihood of unanticipated side-effects. In addition to neutralizing endotoxin, $rBPI_{21}$ exerts antibacterial activity that, in addition to the antibiotic activity of a fluoroquinolone, could potentially curtail further polypharmacy and minimize emergence of resistant species in radiated individuals with numerous reasons for infection. This report provides a foundation for pursuing the mechanisms by which $rBPI_{21}$ impacts radiation toxicity. While optimization of the formulation, dosing regimen, and length of therapy for $rBPI_{21}$ or like agents is similarly desirable, consideration of $rBPI_{21}$ approval for this indication and subsequent stockpiling for combined mitigation therapy in the case of radiation disaster appears warranted.

REFERENCES

1. K. L. Koenig, R. E. Goans, R. J. Hatchett, F. A. Mettler, Jr., T. A. Schumacher, E. K. Noji, D. G. Jarrett, Medical treatment of radiological casualties: current concepts. Ann Emerg Med 45, 643-652 (2005)
2. J. K. Waselenko, T. J. MacVittie, W. F. Blakely, N. Pesik, A. L. Wiley, W. E. Dickerson, H. Tsu, D. L. Confer, C. N. Coleman, T. Seed, P. Lowry, J. O. Armitage, N. Dainiak, Medical management of the acute radiation syndrome: recommendations of the Strategic National Stockpile Radiation Working Group. Ann Intern Med 140, 1037-1051 (2004)
3. G. H. Anno, S. J. Baum, H. R. Withers, R. W. Young, Symptomatology of acute radiation effects in humans after exposure to doses of 0.5-30 Gy. Health Phys 56, 821-838 (1989)
4. H. B. Stone, J. E. Moulder, C. N. Coleman, K. K. Ang, M. S. Anscher, M. H. Barcellos-Hoff, W. S. Dynan, J. R. Fike, D. J. Grdina, J. S. Greenberger, M. Hauer-Jensen, R. P. Hill, R. N. Kolesnick, T. J. Macvittie, C. Marks, W. H. McBride, N. Metting, T. Pellmar, M. Purucker, M. E. Robbins, R. H. Schiestl, T. M. Seed, J. E. Tomaszewski, E. L. Travis, P. E. Wallner, M. Wolpert, D. Zaharevitz, Models for evaluating agents intended for the prophylaxis, mitigation and treatment of radiation injuries. Report of an NCI Workshop, Dec. 3-4, 2003. Radiat Res 162, 711-728 (2004)
5. E. D. Thomas, R. Storb, R. A. Clift, A. Fefer, L. Johnson, P. E. Neiman, K. G. Lerner, H. Glucksberg, C. D. Buckner, Bone-marrow transplantation (second of two parts). N Engl J Med 292, 895-902 (1975)
6. J. G. Kiang, W. Jiao, L. H. Cary, S. R. Mog, T. B. Elliott, T. C. Pellmar, G. D. Ledney, Wound Trauma Increases Radiation-Induced Mortality by Activation of iNOS Pathway and Elevation of Cytokine Concentrations and Bacterial Infection. Radiation Research 173, 319-332 (2010)
7. M. V. Konchalovsky, A. E. Baranov, A. V. Kolganov, Multiple organ involvement and failure: selected Russian radiation accident cases re-visited. BJR Suppl 27, 26-29 (2005)
8. C. P. Miller, C. W. Hammond, The role of infection in radiation injury. Trans Assoc Am Physicians 63, 155-160 (1950)
9. C. W. Hammond, S. K. Anderle, C. P. Miller, Effect of continuous gamma irradiation of mice on their leukocyte counts and susceptibility to bacterial infection. Radiat Res 11, 242-252 (1959)
10. T. Matsuzawa, Survival Time in Germfree Mice after Lethal Whole Body X-Irradiation. Tohoku J Exp Med 85, 257-263 (1965)
11. M. M. McLaughlin, M. P. Dacquisto, D. P. Jacobus, R. E. Horowitz, Effects of the Germfree State on Responses of Mice to Whole-Body Irradiation. Radiat Res 23, 333-349 (1964)
12. M. Onoue, K. Uchida, T. Yokokura, T. Takahashi, M. Mutai, Effect of intestinal microflora on the survival time of mice exposed to lethal whole-body gamma irradiation. Radiat Res 88, 533-541 (1981)
13. P. A. Crawford, J. I. Gordon, Microbial regulation of intestinal radiosensitivity. Proc Natl Acad Sci USA 102, 13254-13259 (2005)
14. I. Brook, R. I. Walker, T. J. MacVittie, Effect of antimicrobial therapy on bowel flora and bacterial infection in irradiated mice. Int J Radiat Biol Relat Stud Phys Chem Med 53, 709-716 (1988)
15. I. Brook, G. D. Ledney, Quinolone therapy in the prevention of endogenous and exogenous infection after irradiation. J Antimicrob Chemother 33, 777-784 (1994)
16. K. Kim, J. M. Pollard, A. J. Norris, J. T. McDonald, Y. Sun, E. Micewicz, K. Pettijohn, R. Damoiseaux, K. S. Iwamoto, J. W. Sayre, B. D. Price, R. A. Gatti, W. H. McBride, High-throughput screening identifies two classes of antibiotics as radioprotectors: tetracyclines and fluoroquinolones. Clin Cancer Res 15, 7238-7245 (2009)
17. E. Ainsworth, From endotoxins to newer immunomodulators: survival-promoting effects of microbial polysaccharide complexes in irradiated animals. Pharmacology & Therapeutics 39, 223-241 (1988)
18. S. S. Boggs, S. M. Wilson, W. W. Smith, Effects of Endotoxin on Hematopoiesis in Irradiated and Nonirradiated W/Wv Mice. Radiation Research 56, 481-493 (1973)
19. L. G. Burdelya, V. I. Krivokrysenko, T. C. Tallant, E. Strom, A. S. Gleiberman, D. Gupta, O. V. Kurnasov, F. L. Fort, A. L. Osterman, J. A. Didonato, E. Feinstein, A. V. Gudkov, An agonist of toll-like receptor 5 has radioprotective activity in mouse and primate models. Science 320, 226-230 (2008)
20. C. D. Packey, M. A. Ciorba, Microbial influences on the small intestinal response to radiation injury. Curr Opin Gastroenterol 26, 88-94 (2010)
21. M. Vijay-Kumar, J. D. Aitken, C. J. Sanders, A. Frias, V. M. Sloane, J. Xu, A. S. Neish, M. Rojas, A. T. Gewirtz, 21. Flagellin treatment protects against chemicals, bacteria, viruses, and radiation. J Immunol 180, 8280-8285 (2008)
22. R. E. Roses, M. Xu, G. K. Koski, B. J. Czerniecki, Radiation therapy and Toll-like receptor signaling: implications for the treatment of cancer. Oncogene 27, 200-207 (2008)
23. G. R. Hill, J. M. Crawford, K. R. Cooke, Y. S. Brinson, L. Pan, J. L. Ferrara, Total body irradiation and acute graft-versus-host disease: the role of gastrointestinal damage and inflammatory cytokines. Blood 90, 3204-3213 (1997)
24. B. Beutler, E. T. Rietschel, Innate immune sensing and its roots: the story of endotoxin. Nat Rev Immunol 3, 169-176 (2003)
25. R. S. Munford, Sensing gram-negative bacterial lipopolysaccharides: a human disease determinant? Infect Immun 76, 454-465 (2008)
26. T. L. Gioannini, J. P. Weiss, Regulation of interactions of Gram-negative bacterial endotoxins with mammalian cells. Immunol Res 39, 249-260 (2007)
27. J. C. Marshall, P. M. Walker, D. M. Foster, D. Harris, M. Ribeiro, J. Paice, A. D. Romaschin, A. N. Derzko, Measurement of endotoxin activity in critically ill patients using whole blood neutrophil dependent chemiluminescence. Crit Care 6, 342-348 (2002)
28. V. Bazil, J. L. Strominger, Shedding as a mechanism of down-modulation of CD14 on stimulated human monocytes. J Immunol 147, 1567-1574 (1991)
29. C. Marsik, F. Mayr, F. Cardona, U. Derhaschnig, O. F. Wagner, B. Jilma, Endotoxaemia modulates Toll-like receptors on leucocytes in humans. British Journal of Haematology. 121(4), 653-656 (2003)
30. P. Crenn, B. Messing, L. Cynober, Citrulline as a biomarker of intestinal failure due to enterocyte mass reduction. Clin Nutr 27, 328-339 (2008)
31. W. J. van der Velden, A. H. Herbers, T. Feuth, N. P. Schaap, J. P. Donnelly, N. M. Blijlevens, Intestinal damage determines the inflammatory response and early complications in patients receiving conditioning for a stem cell transplantation. PLoS One 5, e15156 (2010)
32. Y. Wang, B. A. Schulte, A. C. LaRue, M. Ogawa, D. Thou, Total body irradiation selectively induces murine hematopoietic stem cell senescence. Blood 107, 358-366 (2006)
33. R. J. Bauer, N. Wedel, N. Havrilla, M. White, A. Cohen, S. F. Carroll, Pharmacokinetics of a recombinant modified amino terminal fragment of bactericidal/permeability-increasing protein (rBPI21) in healthy volunteers. J Clin Pharmacol 39, 1169-1176 (1999)
34. D. Demetriades, J. S. Smith, L. E. Jacobson, M. Moncure, J. Minei, B. J. Nelson, P. J. Scannon, Bactericidal/permeability-increasing protein (rBPI21) in patients with hemorrhage due to trauma: results of a multicenter phase II clinical trial. rBPI21 Acute Hemorrhagic Trauma Study Group. J Trauma 46, 667-676; discussion 676-667 (1999)
35. B. P. Giroir, P. A. Quint, P. Barton, E. A. Kirsch, L. Kitchen, B. Goldstein, B. J. Nelson, N. J. Wedel, S. F. Carroll, P. J. Scannon, Preliminary evaluation of recombinant amino-terminal fragment of human bactericidal/permeability-increasing protein in children with severe meningococcal sepsis. Lancet 350, 1439-1443 (1997)
36. B. P. Giroir, P. J. Scannon, M. Levin, Bactericidal/permeability-increasing protein—lessons learned from the phase III, randomized, clinical trial of rBPI21 for adjunctive treatment of children with severe meningococcemia. Crit Care Med 29, S130-135 (2001)
37. M. Levin, P. A. Quint, B. Goldstein, P. Barton, J. S. Bradley, S. D. Shemie, T. Yeh, S. S. Kim, D. P. Cafaro, P. J. Scannon, B. P. Giroir, Recombinant bactericidal/permeability-increasing protein (rBPI21) as adjunctive treatment for children with severe meningococcal sepsis: a randomised trial. rBPI21 Meningococcal Sepsis Study Group. [see comment]. Lancet 356, 961-967 (2000)
38. M. A. von der Mohlen, A. N. Kimmings, N. I. Wedel, M. L. Mevissen, J. Jansen, N. Friedmann, T. J. Lorenz, B. J. Nelson, M. L. White, R. Bauer, et al., Inhibition of endotoxin-induced cytokine release and neutrophil activation in humans by use of recombinant bactericidal/permeability-increasing protein. J Infect Dis 172, 144-151 (1995)
39. M. A. von der Mohlen, S. J. van Deventer, M. Levi, B. van den Ende, N. I. Wedel, B. J. Nelson, N. Friedmann, J. W. ten Cate, Inhibition of endotoxin-induced activation of the coagulation and fibrinolytic pathways using a recombinant endotoxin-binding protein (rBPI23). Blood 85, 3437-3443 (1995)
40. M. J. Wiezer, S. I. Langendoen, C. Meijer, R. J. Bauer, M. L. White, S. F. Carroll, S. Meyer, L. G. Thijs, P. A. van Leeuwen, Pharmacokinetics of a recombinant amino terminal fragment of bactericidal/permeability increasing protein (rBPI21) after liver surgery in rats and humans. Shock 10, 161-166; discussion 167-168 (1998)
41. M. J. Wiezer, C. Meijer, C. Sietses, H. A. Prins, M. A. Cuesta, R. H. Beelen, S. Meijer, P. A. van Leeuwen, Bactericidal/permeability-increasing protein preserves leukocyte functions after major liver resection. Ann Surg 232, 208-215 (2000)
42. P. B. Iannini, The safety profile of moxifloxacin and other fluoroquinolones in special patient populations. Curr Med Res Opin 23, 1403-1413 (2007)
43. U. B. Schaad, Fluoroquinolone antibiotics in infants and children. Infect Dis Clin North Am 19, 617-628 (2005)
44. A. Baranov, R. P. Gale, A. Guskova, E. Piatkin, G. Selidovkin, L. Muravyova, R. E. Champlin, N. Danilova, L. Yevseeva, L. Petrosyan, Bone marrow transplantation after the Chernobyl nuclear accident. N Engl J Med 321, 205-212 (1989)
45. R. Champlin, The role of bone marrow transplantation for nuclear accidents: implications of the Chernobyl disaster. Semin Hematol 24, 1-4 (1987)
46. N. Dainiak, R. C. Ricks, The evolving role of haematopoietic cell transplantation in radiation injury: potentials and limitations. BJR Suppl 27, 169-174 (2005)
47. J. S. Greenberger, Radioprotection. In Vivo 23, 323-336 (2009)
48. I. Thornley, L. E. Lehmann, L. Sung, C. Holmes, J. M. Spear, L. Brennan, M. Vangel, L. J. Bechard, P. Richardson, C. Duggan, E. C. Guinan, A multiagent strategy to decrease regimen-related toxicity in children undergoing allogeneic hematopoietic stem cell transplantation. Biol Blood Marrow Transplant 10, 635-644 (2004)
49. P. Armand, S. Gannamaneni, H. T. Kim, C. S. Cutler, V. T. Ho, J. Koreth, E. P. Alyea, A. S. LaCasce, E. D. Jacobsen, D. C. Fisher, J. R. Brown, G. P. Canellos, A. S. Freedman, R. J. Soiffer, J. H. Antin, Improved survival in lymphoma patients receiving sirolimus for graft-versus-host disease prophylaxis after allogeneic hematopoietic stem-cell transplantation with reduced-intensity conditioning. J Clin Oncol 26, 5767-5774 (2008)
50. O. Levy, K. A. Zarember, R. M. Roy, C. Cywes, P. J. Godowski, M. R. Wessels, Selective impairment of TLR-mediated innate immunity in human newborns: neonatal blood plasma reduces monocyte TNF-alpha induction by bacterial lipopeptides, lipopolysaccharide, and imiquimod, but preserves the response to R-848. J Immunol 173, 4627-4634 (2004)

51. K. E. Nathe, R. Parad, L. J. Van Marler, C. A. Lund, E. E. Suter, S. Hernandez-diaz, E. B. Boush, E. Ikonomu, L. Gallington, J. A. Morey, A. M. Zeman, M. McNamara, O. Levy, Endotoxin-directed innate immunity in tracheal aspirates of mechanically ventilated human neonates. Pediatr Res 66, 191-196 (2009)

52. P. Zhang, D. A. Welsh, R. W. Siggins, 2nd, G. J. Bagby, C. E. Raasch, K. I. Happel, S. Nelson, Acute alcohol intoxication inhibits the lineage—c-kit+ Sca-1+ cell response to *Escherichia coli* bacteremia. J Immunol 182, 1568-1576 (2009)

We claim:

1. A method for bone marrow recovery in a subject, the method comprising: administering to a subject in need thereof bactericidal/permeability increasing protein (BPI) and/or its congeners in an amount effective for bone marrow recovery in the subject.

2. The method of claim 1, wherein the subject has a deficiency in one or more hematopoietic cell types or lineages.

3. The method of claim 1, wherein the subject has a hematopoietic deficiency comprising lymphopenia, myelopenia, leukopenia, neutropenia, erythropenia, megakaryopenia, a deficiency in platelets, a deficiency in monocytes, a deficiency in lymphocytes, a deficiency in erythrocytes, deficiency in neutrophils, a deficiency in T cells, a deficiency in granulocytes, and/or a deficiency in dendritic cells.

4. The method of claim 3, wherein the deficiency in one or more hematopoietic cell types or lineages results from exposure to radiation, chemoradiotherapy, radiotherapy, disease, toxin or drug or biologic-mediated therapy.

5. The method of claim 1, wherein BPI congeners is selected from the group consisting of rBPI$_{21}$, rBPI$_{23}$, rBPI$_{50}$, rBPI(10-193)ala$^{132}$ and a N-terminal fragment of BPI having a molecular weight approximately between 20 to 25 kD.

6. The method of claim 1, further comprising administering an antibiotic.

7. The method of claim 6, wherein the antibiotic is a quinolone antibiotic.

8. The method of claim 7, wherein the quinolone antibiotic is selected from the group consisting of moxifloxacin, ciprofloxacin, levofloxacin, garenoxacin, and delafloxacin.

9. The method of claim 1, wherein BPI and/or its congeners is administered orally, intravenously, or subcutaneously.

10. A method for stimulating hematopoiesis in a subject, the method comprising: administering to a subject in need thereof bactericidal/permeability increasing protein (BPI) and/or its congeners in an amount effective to stimulate hematopoiesis in the subject.

11. The method of claim 10, wherein the subject has a deficiency in one or more hematopoietic cell types or lineages.

12. The method of claim 10, wherein the subject has a hematopoietic deficiency comprising lymphopenia, myelopenia, leukopenia, neutropenia, erythropenia, megakaryopenia, a deficiency in platelets, a deficiency in monocytes, a deficiency in lymphocytes, a deficiency in erythrocytes, deficiency in neutrophils, a deficiency in T cells, a deficiency in granulocytes, and/or a deficiency in dendritic cells.

13. The method of claim 12, wherein the deficiency in one or more hematopoietic cell types or lineages results from exposure to radiation, chemoradiotherapy, radiotherapy, disease, toxin or drug or biologic-mediated therapy.

14. The method of claim 10, wherein BPI congeners is selected from the group consisting of rBPI$_{21}$, rBPI$_{23}$, rBPI$_{50}$, rBPI(10-193)ala$^{132}$ and a N-terminal fragment of BPI having a molecular weight approximately between 20 to 25 kD.

15. The method of claim 10, further comprising administering an antibiotic.

16. The method of claim 15, wherein the antibiotic is a quinolone antibiotic.

17. The method of claim 16, wherein the quinolone antibiotic is selected from the group consisting of moxifloxacin, ciprofloxacin, levofloxacin, garenoxacin, and delafloxacin.

18. The method of claim 10, wherein BPI and/or its congeners is administered orally, intravenously, or subcutaneously.

* * * * *

UNITED STATES PATENT AND TRADEMARK OFFICE
CERTIFICATE OF CORRECTION

| | | |
|---|---|---|
| PATENT NO. | : 9,770,484 B2 | Page 1 of 1 |
| APPLICATION NO. | : 15/169969 | |
| DATED | : September 26, 2017 | |
| INVENTOR(S) | : Eva Guinan et al. | |

It is certified that error appears in the above-identified patent and that said Letters Patent is hereby corrected as shown below:

In the Specification

At Column 1, Line 7, the text:
"This application is a divisional of Serial No. 14/009,201, filed October 1, 2013, which is a national stage filing under 35 U.S.C. § 371 of international application PCT/US2012/032288, filed April 5, 2012, which was published under PCT Article 21(2) in English, and claims the benefit under 35 U.S.C. § 119(e) of U.S. provisional application serial number 61/471,896, filed April 5, 2011 the disclosures of which are incorporated by reference herein in their entireties."
Should be replaced with the text:
--This application is a divisional of Serial No. 14/009,201, filed December 17, 2013, which is a national stage filing under 35 U.S.C. § 371 of international application PCT/US2012/032288, filed April 5, 2012, which was published under PCT Article 21(2) in English, and claims the benefit under 35 U.S.C. § 119(e) of U.S. provisional application serial number 61/471,896, filed April 5, 2011 the disclosures of which are incorporated by reference herein in their entireties.--

At Column 1, Line 19, the text:
"This invention was made with government support under grant numbers U19 AI067751 awarded by The National Institutes of Health and HR0011-08-1-0011 awarded by The Defense Advanced Research Projects Agency. The government has certain rights in the invention."
Should be replaced with the text:
--This invention was made with government support under grant number U19 AI067751 awarded by The National Institutes of Health and grant numbers HR0011-08-1-0011 and HR0011-12-1-0014 awarded by The Defense Advanced Research Projects Agency. The government has certain rights in the invention.--

Signed and Sealed this
Sixth Day of March, 2018

Andrei Iancu
*Director of the United States Patent and Trademark Office*